United States Patent
Richter

[11] Patent Number: 6,114,049
[45] Date of Patent: *Sep. 5, 2000

[54] STENT FABRICATION METHOD

[75] Inventor: Jacob Richter, Tel Aviv, Israel

[73] Assignee: Medinol Ltd., Tel Aviv, Israel

[*] Notice: This patent is subject to a terminal disclaimer.

[21] Appl. No.: 09/109,772

[22] Filed: Jul. 2, 1998

Related U.S. Application Data

[62] Division of application No. 08/774,970, Dec. 16, 1996, Pat. No. 5,906,759.

[51] Int. Cl.[7] ................ A61M 29/00; A61F 2/06
[52] U.S. Cl. ................. 428/571; 428/573; 428/577
[58] Field of Search ................ 428/577, 596, 428/571, 572, 573, 574, 575, 583, 600, 582

[56] References Cited

U.S. PATENT DOCUMENTS

| | | | |
|---|---|---|---|
| 728,178 | 5/1903 | Schmeltzer | 72/51 |
| 1,237,195 | 8/1917 | Gargiulo | 72/398 |
| 1,429,328 | 9/1922 | Domizi | 72/51 |
| 1,629,813 | 5/1927 | Stevenson | 72/51 |
| 3,802,239 | 4/1974 | Karmann et al. | 72/51 |
| 4,152,573 | 5/1979 | Saurin et al. | 72/121.63 |
| 4,513,596 | 4/1985 | Usher | 219/51 |
| 4,680,031 | 7/1987 | Alonso | 72/2 |
| 4,776,337 | 10/1988 | Palmaz | 128/343 |
| 5,026,967 | 6/1991 | Bell et al. | 219/121.64 |
| 5,304,200 | 4/1994 | Spaulding | 606/198 |
| 5,421,955 | 6/1995 | Lau et al. | 216/48 |
| 5,443,500 | 8/1995 | Sigwart | 623/1 |
| 5,449,372 | 9/1995 | Schmaltz et al. | 606/198 |
| 5,514,154 | 5/1996 | Lau et al. | 606/195 |
| 5,540,712 | 7/1996 | Kleshinski | 606/198 |
| 5,540,713 | 7/1996 | Schnepp-Pesch et al. | 606/198 |
| 5,618,299 | 4/1997 | Khosravi et al. | 606/198 |
| 5,716,396 | 2/1998 | Williams, Jr. | 623/1 |
| 5,755,781 | 5/1998 | Jayaraman | 623/1 |
| 5,800,526 | 9/1998 | Anderson et al. | 623/1 |
| 5,807,404 | 9/1998 | Richter | 623/1 |
| 5,836,964 | 11/1998 | Richter et al. | 606/194 |
| 5,843,164 | 12/1998 | Frantzen et al. | 623/1 |
| 5,906,759 | 5/1999 | Richter | 219/121.63 |
| 5,907,893 | 6/1999 | Zadno-Azizi et al. | 29/6.1 |

FOREIGN PATENT DOCUMENTS

| | | |
|---|---|---|
| 0 709 067 | 5/1996 | European Pat. Off. . |
| 43 03 181 | 8/1994 | Germany . |

*Primary Examiner*—John J. Zimmerman
*Attorney, Agent, or Firm*—Kenyon & Kenyon

[57] ABSTRACT

A stent and a method for fabricating the stent are disclosed. The stent has an originally flat pattern and connection points where the sides of the flat pattern are joined. The method includes the steps of a) cutting a stent pattern into a flat piece of metal thereby to produce a metal pattern, b) deforming the metal pattern so as to cause two opposing sides to meet, and c) joining the two opposing sides at least at one point. Substantially no portion of the stent projects into the lumen of the stent when the stent is expanded against the internal wall of a blood vessel.

7 Claims, 23 Drawing Sheets

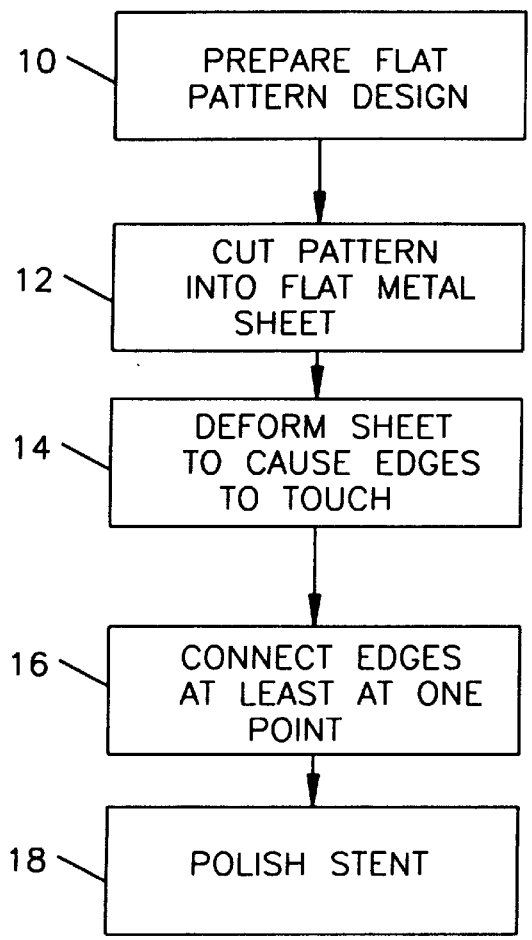
FIG. 1
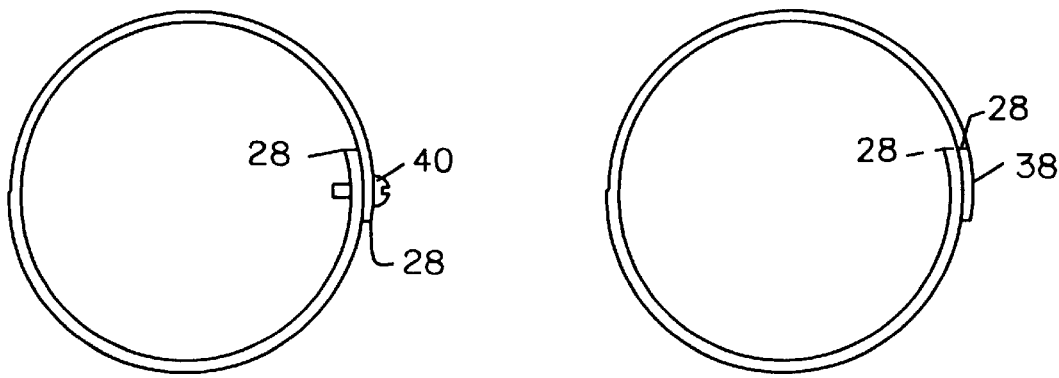
FIG. 6
FIG. 5A

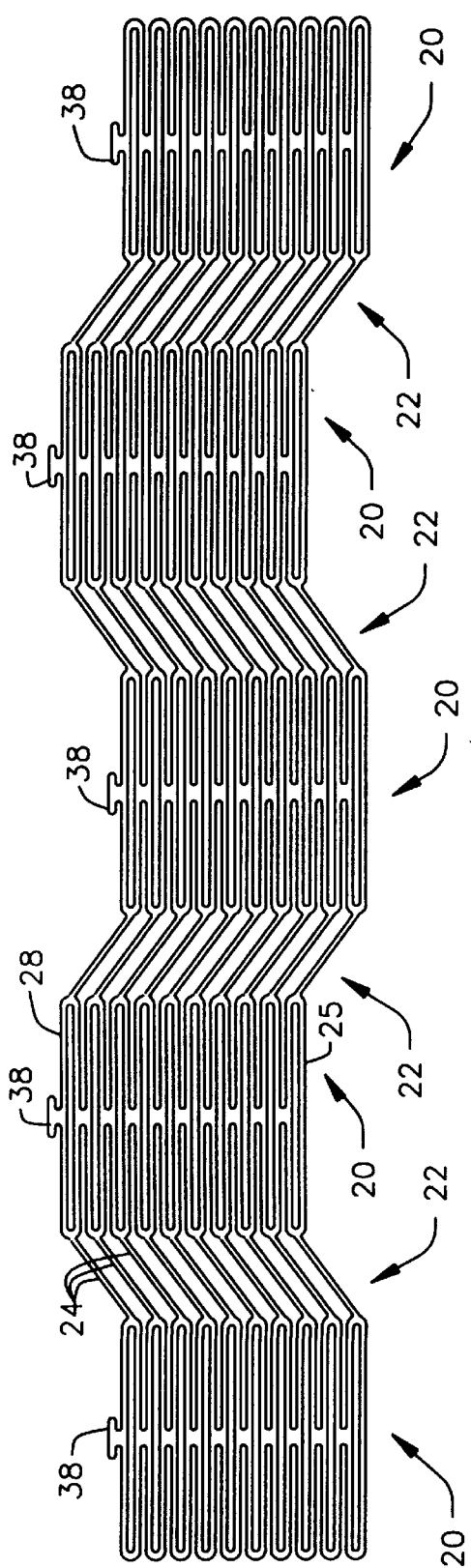
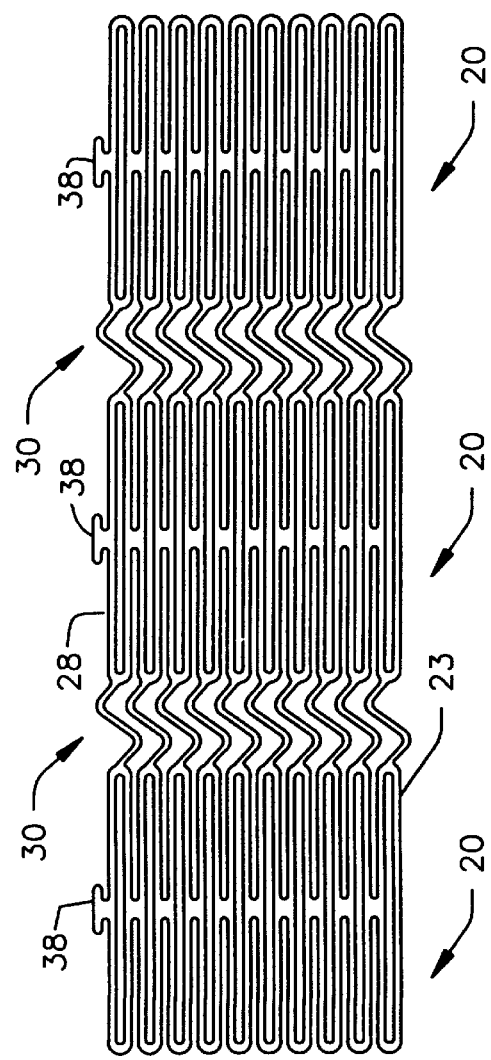

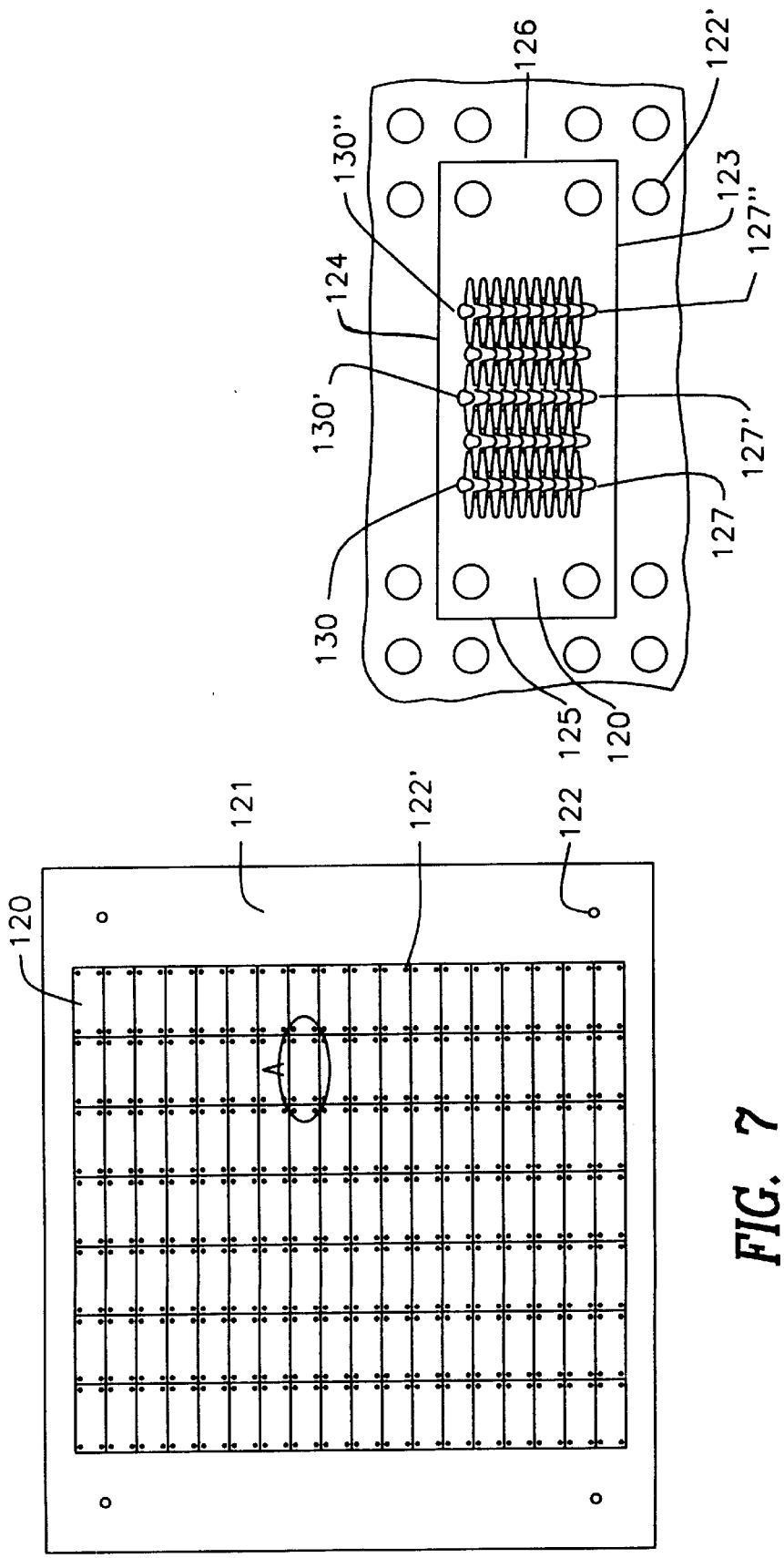

STENT FABRICATION METHOD

This is a divisional of Ser. No. 08/774,970 filed Dec. 26, 1996, now U.S. Pat. No. 5,906,759.

FIELD OF THE INVENTION

The present invention relates generally to methods and apparatus of fabricating stents.

BACKGROUND OF THE INVENTION

Stents are known in the art. They are typically formed of a cylindrical metal mesh which can expand when pressure is internally applied. Alternatively, they can be formed of wire wrapped into a cylindrical shape.

As described in U.S. Pat. No. 4,776,337 to Palmaz, the cylindrical metal mesh shape is produced by laser cutting a thin walled metal tube. The laser cuts away all but the lines and curves of the mesh.

The method of U.S. '337 is applicable for relatively large mesh shapes and for meshes whose lines are relatively wide. However, for more delicate and/or intricate shapes, the spot size of the laser is too large.

SUMMARY OF THE PRESENT INVENTION

It is, therefore, an object of the present invention to provide a stent fabrication method which can produce stents with relatively intricate and/or delicate designs.

The method involves first creating a flat version of the desired stent pattern from a piece of thin sheet metal. The flat pattern can be produced through any suitable technique, such as etching the design into the sheet metal, or by cutting with a very fine laser, should one become commercially available or by any other technique.

Once the sheet metal has been cut, it is deformed so as to cause its edges to meet. To create a cylindrical stent from a flat, roughly rectangular metal pattern, the flat metal is rolled until the edges meet. The locations where edges meet are joined together, such as by spot welding. Afterwards, the stent is polished, either mechanically or electrochemically.

It is an object of this invention to provide an apparatus for fabricating a stent, comprising:

a) a platform adapted to receive a flat sheet of metal to be formed into the stent, the flat sheet of metal having a longitudinal axis, a first major surface, a second major surface, a first long side, and a second long side, the first and the second long sides substantially parallel to the longitudinal axis of the sheet;

b) a mandrel having a substantially cylindrical external surface and having a first end and a second end defining a longitudinal axis, the mandrel sized to have a cross-sectional diameter substantially equal to or less than the internal diameter of the stent to be fabricated;

c) means for securing the mandrel against a major surface of the flat sheet of metal; and d) means for deforming the flat sheet of metal against the external surface of the mandrel so that the flat sheet of metal is deformed into a substantially tubular shape, the means for deforming adapted so that the first long side and the second long side remain substantially parallel to each other when the flat sheet of metal is deformed into the tubular shape.

It is another object of this invention to provide and apparatus for fabricating a stent, comprising:

a) a base having a platform adapted to receive a flat sheet of metal to be formed into the stent, the flat sheet of metal having a longitudinal axis, a first major surface, a second major surface, a first long side, and a second long side, the first and the second long sides substantially parallel to the longitudinal axis of the stent;

b) a mandrel having a substantially cylindrical external surface and having a first end and a second end defining a longitudinal axis, the mandrel sized to have a cross-sectional diameter substantially equal to or less than the internal diameter of the stent to be fabricated;

c) means for securing the mandrel against a major surface of the flat sheet of metal;

d) a plurality of deforming blades disposed around the periphery of the mandrel for deforming the flat sheet of metal against the external surface of the mandrel so that the flat sheet of metal is deformed into a substantially tubular shape, the blades disposed between the first end and the second end of the mandrel, each of the deforming blades adapted for independent and selective movement in a first direction toward the mandrel and a second direction away from the mandrel so as to selectively impinge upon the mandrel or upon a portion of the sheet disposed between the mandrel and each of the deforming blades, each of the deforming blades further adapted so that the first long side and the second long side of the sheet remain substantially parallel to each other when the stent is deformed into the tubular shape;

e) means for selectively moving each of the deforming blades in a first direction toward the mandrel and in a second direction away from the mandrel; and f) means for securing the first long side of the sheet to the second long side of the sheet.

It is yet another object of this invention to provide an apparatus for fabricating a stent, comprising: means for securing the first long side of the sheet to the second long side of the sheet.

It is still another object of this invention to provide an apparatus for fabricating a stent, comprising:

a) a base;

b) a sheet receiving area disposed on the base, the area adapted to receive a flat sheet of metal to be formed into the stent, the flat sheet of metal having a longitudinal axis, a first major surface, a second major surface, a first long side, and a second long side, the first and the second long sides substantially parallel to the longitudinal axis;

c) an arm having a first end and a second end, the first end of the arm adapted to selectively retain a mandrel having a substantially cylindrical external surface, the second end of the arm hingedly connected to the base and adapted for movement in a first direction toward the base and in a second direction away from the base and further adapted to secure the mandrel against a major surface of the flat sheet of metal disposed on the stent receiving area disposed on the base, the mandrel sized to have a cross-sectional diameter substantially equal to or less than the internal cross-sectional diameter of the stent to be fabricated;

d) means for deforming the flat piece of metal against the external surface of the mandrel so that the flat sheet of metal is deformed into a substantially tubular shape substantially conforming to the external surface of the mandrel with the first long side and the second long side substantially parallel to each other.

It is yet another object of this invention to provide a stent aligning and welding jig comprising:

a) a base having a first end and a second end, a first wall having a first end and a second end and a first major surface and a second major surface; a second wall having a first end and a second end and a first major surface and a second major surface, the second major surface of the first wall and the first major surface of the second wall defining a longitudinal U-shaped channel having a longitudinal axis in the base, the first wall provided with a plurality of slots defining a plurality of first clamping portions having a top end and a bottom end and a first major surface and a second major surface, each of the first clamping portions provided with a first concave channel disposed at the top end of the second major surface of the first clamping portion and a second concave channel disposed at the bottom end of the second major surface of the first clamping portion, the first and the second concave channels substantially parallel to the longitudinal axis of the U-shaped channel; the first wall of each of the plurality of first clamping portions provided with a compensation slit disposed between the first concave channel and the second concave channel, the compensation slit substantially parallel to the longitudinal axis of the U-shaped channel;

b) a plurality of second clamping portions disposed in the U-shaped channel between the second major surface of the first wall and the first major surface of the second wall, each of the second clamping portions disposed in registry with one of the first clamping portions, each of the second clamping portions having a top end, a bottom end, a first major surface, a second major surface, a first minor surface disposed at the top end, a second minor surface disposed at the bottom end, a third minor surface disposed between the top end and the bottom end, and a fourth minor surface disposed opposite the third minor surface between the top end and the bottom end, each of the second clamping portions provided with a first concave channel disposed at the top end of the first major surface of the second clamping portion and a second concave channel disposed at the bottom end of the first major surface of the second clamping portion, the first and the second concave channels substantially parallel to the longitudinal axis of the U-shaped channel;

c) a biasing means disposed between the first major surface of the second wall and the second major surface of each of the plurality of second clamping portions for biasing the first major surface of each of the second clamping portions against the second major surface of each of the first clamping portions which are in registry with each other;

d) a first mandrel support lever positioning pin projecting from the third minor surface and a second mandrel support lever positioning pin projecting from the fourth minor surface of each of the second clamping portions, the mandrel support lever positioning pins substantially parallel to the longitudinal axis of the U-shaped channel;

e) a biasing control means for selectively controlling the distance between the second major surface of each of the first clamping portions and the first major surface of each of the second clamping portions;

f) a retaining mandrel disposed in the second concave channel of the first wall and the second concave channel in each of the second clamping portions; and g) a mandrel support lever for supporting the stent during the alignment of the first long side of the sheet with the second long side of the sheet, the lever provided with a first mandrel support notch for supporting the first end of the mandrel, a second mandrel support notch for supporting the second end of the mandrel, a first mandrel support lever positioning pin engagement surface for engaging the first mandrel support lever positioning pin and a second mandrel support lever positioning pin engagement surface for engaging the second mandrel support lever positioning pin when the mandrel support lever is disposed on the second wall.

It is still another object of this invention to provide a method of fabricating a stent comprising the steps of:

a) providing a plurality of stent patterns into a flat piece of metal, each of the patterns having a first long side and a second long side, the first long side provided with a plurality of pairs of engagement points, the second long side provided with a plurality of pairs of engagement points, the plurality of pairs of engagement points disposed substantially opposite each other, the engagement points sized and disposed to communicate when the pattern is deformed and rolled into a tubular shape, each pair of the first long side engagement points provided with a bridge disposed between each first long side engagement point comprising the pair, the bridge having a width that is less than the width of the other portions of the stent;

b) disposing a mandrel having a substantially cylindrical external surface and a longitudinal axis between the first long side and the second long side of the sheet, the longitudinal axis substantially parallel to the first long side and the second long side;

c) deforming the pattern into a tubular shape so that the first long side pairs of engagement points contact the second long side pairs of engagement points;

d) cutting the bridge; and e) attaching each of the engagement points to the engagement point with which it is in contact to form the expandable stent.

It is yet another object of this invention to provide a jig for electropolishing a tubular stent, comprising:

a) a base;

b) an electrically conductive first member having a first end connected to the base and a second end adapted to selectively contact the external surface of the tubular stent without damaging the external surface;

c) an electrically non-conductive second member having a first end connected to the base and a second end adapted to be selectively disposed within the longitudinal bore of the stent without damaging the longitudinal bore, the first member and the second member further adapted so as to bias the second end of the second member towards the second end of the first member in an amount sufficient to secure the stent between the first and the second members.

It is still another object to this invention to provide a method of electropolishing a stent, comprising the steps of:

a) mounting a stent on a rack, the rack having a first end and a second end provided with a plurality of stent electropolishing mounts, each of the mounts having a base; an electrically conductive first member having a first end connected to the base and a second end adapted to selectively contact the external surface of the tubular stent without damaging the external surface; an electrically non-conductive second member having a first end connected to the base and a second end adapted to be selectively disposed within the longitudinal bore of the stent without damaging the longitudinal bore, the first member and the second member further adapted so as to bias the second end of the second member towards the second end of the first member in an amount sufficient to secure the stent between the first and the second members;

b) immersing the stent in an electropolishing bath and applying electrical current to the first member for a predetermined period of time; and c) changing the point where the second end of the first member contacts the external surface of the stent prior to the expiration of the predetermined period of time.

It is yet another object of this invention to provide a method of fabricating a stent comprising the steps of:

a) providing a plurality of stent patterns in a flat sheet of metal; each of the patterns having a first long side and a second long side, the first long side provided with a plurality of pairs of engagement points, the second long side provided with a plurality of pairs of engagement points, the plurality of pairs of engagement points disposed substantially opposite each other, the engagement points sized and disposed to communicate when the pattern is deformed and rolled into a tubular shape, each pair of the first long side engagement points provided with a bridge disposed between each first long side engagement point comprising the pair, the bridge having a width that is less than the width of the other portions of the stent;

b) disposing a mandrel having a substantially cylindrical external surface and a longitudinal axis between the first long side and the second long side of the sheet, the longitudinal axis substantially parallel to the first and the second long sides;

c) deforming the pattern into a tubular shape so that the first long side pairs of engagement points contact the second long side pairs of engagement points and allowing a portion of the stent to remain attached to the sheet of metal;

d) cutting the bridge;

e) attaching each of the engagement points to the engagement point with which it is in contact to form the stent;

f) attaching an electrode to the sheet of metal;

g) electropolishing the stent; and f) disconnecting the stent from the sheet.

It is yet another object of this invention to provide a sheet for fabricating a stent having a longitudinal lumen:

a) a flat piece of sheet metal provided with a plurality of stent patterns, each of the patterns having a first long side and a second long side, the first long side provided with a plurality of pairs of engagement points, the second long side provided with a plurality of pairs of engagement points, the plurality of pairs of engagement points disposed substantially opposite each other, the engagement points sized and disposed to communicate when the pattern is deformed and rolled into a tubular shape, each pair of the first long side engagement points provided with a bridge disposed between each first long side engagement point comprising the pair, the bridge having a width that is less than the width of the other portions of the stent.

It is yet another object of this invention to provide a method for fabricating a stent having a longitudinal lumen comprising the steps of:

a.) constructing an apparatus comprising:

a) a laser housing;

b) a laser disposed within and selectively movable within the housing;

c) a movable table having a first end and a second end and adapted for selective movement into and out of the laser housing the table adapted so that when the first end of the table is disposed within the laser housing the second end of the table is disposed outside of the housing and when the second end of the table is disposed within the laser housing the first end of the table is disposed outside of the laser housing;

d) a plurality of stent folders disposed at the first end of the table and a plurality of stent folders disposed at the second end of the table, each of the stent folders comprising:

a) a base having a platform adapted to receive a flat sheet of metal to be formed into the stent, the flat sheet of metal having a longitudinal axis, a first major surface, a second major surface, a first long side, and a second long side, the first and the second long sides substantially parallel to the longitudinal axis, the sheet provided with a plurality of alignment of apertures;

b) a plurality of alignment pins projecting from each of the platforms, the pins sized to engage the alignment apertures and align the sheet on the platform;

c) a mandrel having a substantially cylindrical external surface and having a first end, a second end, and a longitudinal axis, the mandrel sized to have a cross-sectional diameter substantially equal to or less than the internal diameter of the stent to be fabricated, the platform provided with a first concave recess adapted to receive the first end of the mandrel and a second concave recess adapted to receive the second end of the mandrel;

d) a hingedly connected arm adapted for movement in a first direction toward the platform and in a second direction away from the platform for securing the mandrel against a major surface of the flat sheet of metal;

e) a first deforming blade provided with a first deforming blade tip; a second deforming blade provided with a second deforming blade tip; a third deforming blade provided with a third deforming blade tip; a fourth deforming blade provided with a fourth deforming blade tip; a fifth deforming blade provided with a fifth deforming blade tip; and a sixth deforming blade provided with a sixth deforming blade tip, the blades disposed around the external surface of the mandrel, the deforming blade tips adapted to deform the flat sheet of metal against the external surface of the mandrel so that the flat sheet of metal is deformed into a substantially tubular shape substantially conforming to the external surface, the deforming blades disposed between the first end and the second end of the mandrel, each of the deforming blades adapted for independent and selective movement in a first direction toward the mandrel and a second direction away from the mandrel so as to selectively impinge the deforming blade tips against the mandrel or against a portion of the sheet disposed between the mandrel and each of the deforming blade tips, each of the deforming blades further adapted so that the first long side and the second long side of the sheet remain substantially parallel to each other when the stent is deformed into the tubular shape, the third and the sixth deforming blade tips provided with a plurality of scalloped laser apertures, the apertures sized and disposed to permit the third and the sixth deforming blade tips to secure the first long side and the second long side against the external surface of the mandrel while providing the laser access to predetermined portions of the first long side and the second long side of the sheet in order to weld the first long side to the second long side;

f) a first motor connected to the first deforming blade; a second motor connected to the second deforming blade; a third motor connected to the third deforming blade; a fourth motor connected to the fourth deforming blade; a fifth motor connected to the fifth deforming blade; and a sixth motor connected to the sixth deforming blade, each of the motors adapted for selectively moving each of the deforming blades to which it is connected in a first direction toward the mandrel and in a second direction away from the mandrel; and g) a computer for controlling: the sequence which the first end of the table and the second end of the table are disposed within the laser housing; for controlling the sequence and degree to which each of the plurality of deforming blade tips impinges upon the mandrel or a portion of the sheet disposed between the mandrel and each of the deforming blade tips; and for controlling the sequence, pattern, location, and amount of energy the laser applies to each of the first and the second long sides of each of the sheets disposed on each of the plurality of stent folders;

b.) cutting a plurality of stent patterns into a flat piece of metal, each of the patterns having a first major surface and a second major surface, a first long side and a second long side, the first long side provided with a plurality of pairs of engagement points, the second long side provided with a plurality of pairs of engagement points, the plurality of pairs of engagement points disposed substantially opposite each other, the engagement points sized and disposed to communicate when the pattern is deformed and rolled into a tubular shape, each pair of the first long side engagement points provided with a bridge disposed between each first long side engagement point comprising the pair, the bridge having a width that is less than the width of the other portions of the stent, the sheet provided with a plurality of alignment apertures sized and disposed to engage the alignment pins on the base;

c.) disposing the sheet on the base so that the first major surface of the sheet is in contact with the base;

d.) disposing a mandrel having a substantially cylindrical external surface and a longitudinal axis against the second major surface of the sheet between the first long side and the second long side of the sheet, the longitudinal axis substantially parallel to the first long side and the second long side;

e.) deforming the pattern into a tubular shape so that the first long side pairs of engagement points contact the second long side pairs of engagement points the deforming step comprising the steps of:

a) actuating the sixth deforming blade motor so that the sixth deforming blade motor moves the sixth deforming blade in the first direction in an amount sufficient for the sixth deforming blade tip to contact the external surface of the mandrel so as to secure the mandrel against the sheet;

b) actuating the first deforming blade motor so that the first blade deforming motor moves the first deforming blade in the first direction in an amount sufficient for the first blade deforming tip to contact the first major surface of the sheet and deform the sheet against the external surface of the mandrel;

c) actuating the second deforming blade motor so that the second deforming blade motor moves the second deforming blade in the first direction in an amount sufficient for the second deforming blade tip to contact the first major surface of the sheet and deform the sheet against the external surface of the mandrel;

d) actuating the third deforming blade motor so that the third deforming blade motor moves the second deforming blade in the first direction in an amount sufficient for the third deforming blade tip to contact the first major surface of the sheet and deform the sheet against the external surface of the mandrel while actuating the sixth deforming blade motor so that the sixth deforming blade moves in the second direction away from the mandrel;

e) actuating the fourth deforming blade motor so that the fourth deforming blade motor moves the fourth deforming blade tip in the first direction in an amount sufficient for the fourth deforming blade tip to contact the first major surface of the sheet and deform the sheet against the external surface of the mandrel;

f) actuating the fifth deforming blade motor so that the fifth deforming blade motor moves the fifth deforming blade in the first direction in an amount sufficient for the fifth deforming blade tip to contact the first major surface of the sheet and deform the sheet against the external surface of the mandrel;

g) actuating the sixth deforming blade motor so that the sixth deforming blade motor moves the second deforming blade in the first direction in an amount sufficient for the second deforming blade tip to contact the first major surface of the sheet and deform the sheet against the external surface of the mandrel;

h) simultaneously actuating the third and sixth deforming blade motors so that the third and sixth deforming blade motors move the third and sixth deforming blades in the first direction in an amount sufficient for the third and sixth deforming blade tips to contact the first major surface of the sheet and deform the sheet against the external surface of the mandrel;

d) utilizing the laser in cutting the bridge; and e) utilizing the laser in welding each of the engagement points to the engagement point with which it is in contact to form the expandable stent.

It is a further object of this invention to provide a stent having a longitudinal lumen, comprising: a first long side and a second long side, the first long side provided with a plurality of pairs of engagement points, the second long side provided with a plurality of pairs of engagement points, the plurality of pairs of first long side engagement points and the plurality of pairs of second long side engagement points disposed substantially opposite each other and connected to each other via a weld, the weld wider than the other portions of the stent.

BRIEF DESCRIPTION OF THE DRAWINGS

The present invention will be understood and appreciated more fully from the following detailed description taken in conjunction with the drawings in which:

FIG. 1 is a flow chart illustration of the stent fabrication method of the present invention;

FIGS. 2A, 2B and 2C are illustrations of three alternative stent patterns to be etched, in accordance with the method of FIG. 1, into a flat sheet of metal;

FIGS. 5A and 5B are side and top view illustrations, respectively, of one connection location of the stent of FIG. 4;

FIG. 6 is a side view illustration of one connection location of the stent of FIG. 4 which is connected in a nail-like manner;

FIG. 7 shows a piece of sheet metal with a plurality of patterns made in accordance with the invention;

FIG. 8 shows a detailed view of one of the patterns shown in FIG. 7;

DETAILED DESCRIPTION OF A PREFERRED EMBODIMENT

Reference is now made to FIG. 1, which illustrates the stent fabrication method of the present invention and to FIGS. 2A, 2B, 2C, 3 and 4 which are useful in understanding the method of FIG. 1.

In the stent fabrication method of the present invention, a stent designer first prepares a drawing of the desired stent pattern in a flat format (step 10).

Figure 2C:
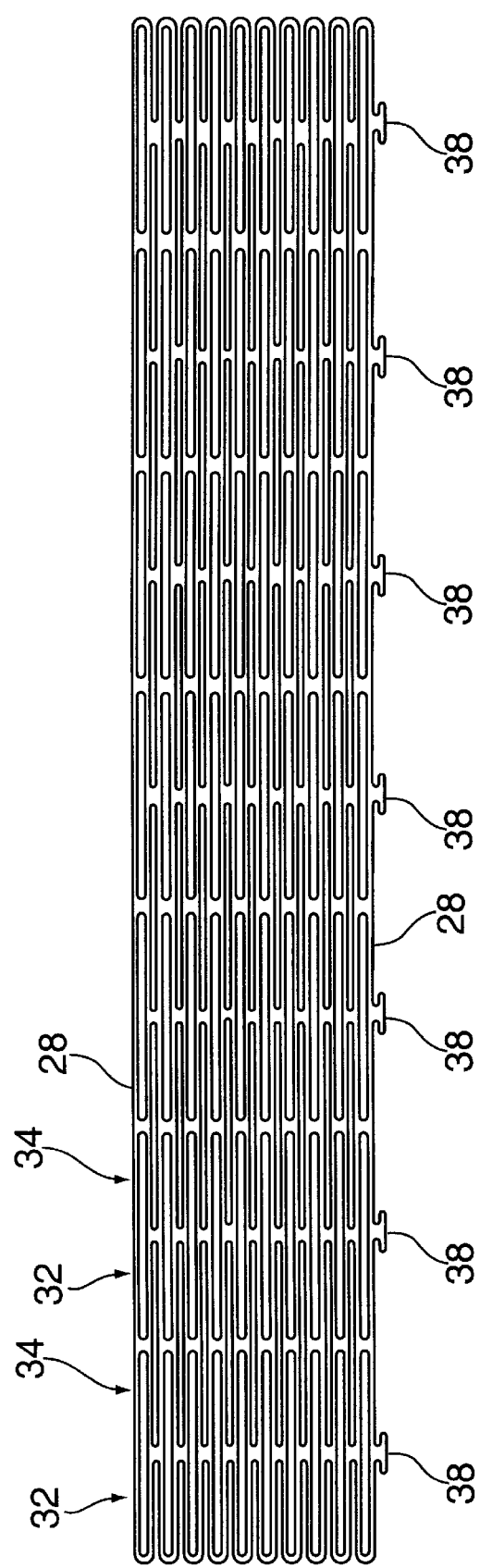

FIGS. 2A, 2B and 2C illustrate three exemplary stent pattern designs. The pattern of FIG. 2A has two types of sections 20 and 22. Each section 20 has two opposing periodic patterns and each section 22 has a plurality of connecting lines 24. The pattern of FIG. 2A can be formed of any size; a preferable size is to have each section 20 be between 1 and 6 mm wide and each section 22 have connecting lines 24 of 1–6 mm long. At such sizes, the pattern of FIG. 2A cannot be cut using a laser cutting system.

The pattern of FIG. 2B is similar to that of FIG. 2A in that it also has sections 20 of opposing periodic patterns. The pattern of FIG. 2B also has connecting sections, labeled 30, which have a Z shape.

The pattern of FIG. 2C has no connecting sections. Instead, it has a series of alternating patterns, labeled 32 and 34.

The patterns of FIGS. 2A, 2B and 2C optionally also have a plurality of small protrusions 38 which are useful in forming the stent, as described hereinbelow.

Returning to FIG. 1, in step 12, the stent pattern is cut into a flat piece of metal ("sheet metal"). The metal can be any type of biocompatible material, such as stainless steel, or a material which is plated with a biocompatible material. The cutting operation can be implemented in any of a number of ways, such as by etching, or by cutting with a fine cutting tool, or by cutting with a very fine laser, should one become commercially available.

If step 12 is implemented with etching, then, the process is designed to cut through the sheet metal. This process is known; however, for the purposes of completeness, it will be briefly described hereinbelow.

The drawing of the pattern is reduced and printed onto a transparent film. Since it is desired to cut completely through the metal, the drawing is printed onto two films which are joined together in a few places along their edges. The sheet metal is covered, on both sides, with a layer of photoresist and placed between the two transparent, printed films. The structure is illuminated on both sides which causes the portions of the photoresist which receive the light (which are all the empty spaces in the pattern, such as spaces 26 of FIG. 2A) to change properties.

The sheet metal is placed into acid which eats away those portions of the photoresist which changes properties. The sheet metal is then placed into an etching solution which etches away all material on which there is no photoresist-removing solution which removes the photoresist, leaving the metal having the desired stent pattern.

Figure 3:
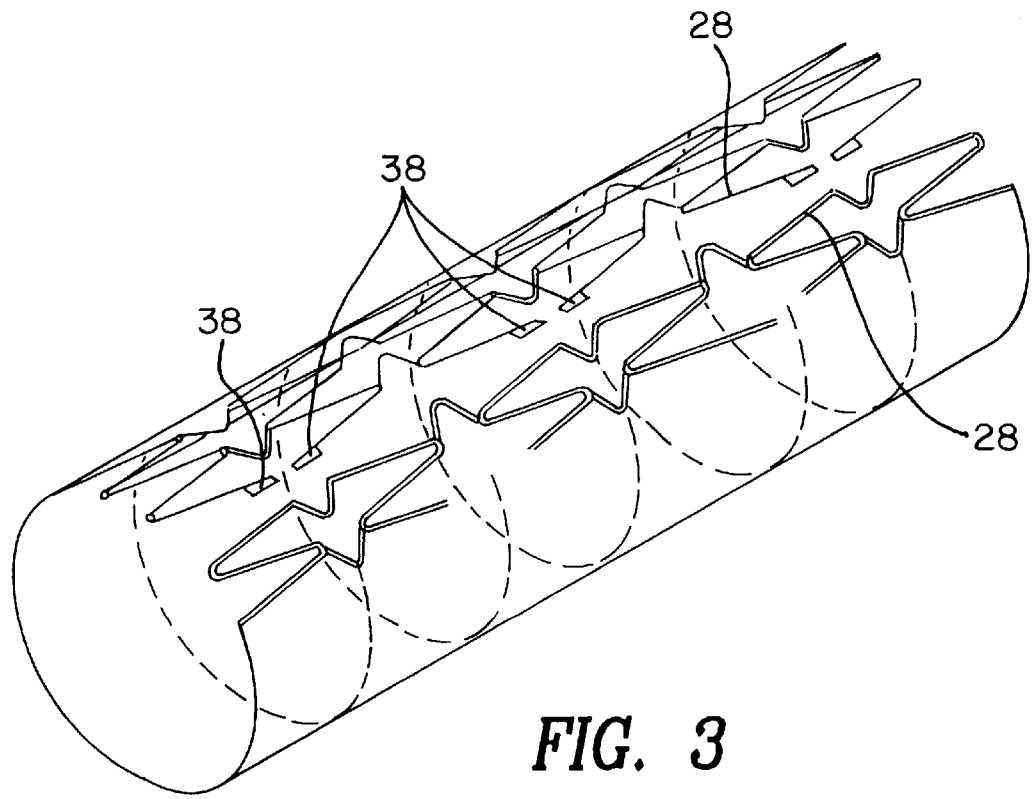
FIG. 3 is an isometric illustration of a stent being deformed, useful in understanding the method of FIG. 1.

In step 14, the metal pattern is deformed so as to cause its long sides (labeled 28 in FIGS. 2A, 2B and 2C) to meet other. FIG. 3 illustrates the deformation process. For cylindrical stents, the deformation process is a rolling process, as shown.

If the protrusions 38 have been produced, after deformation of the metal pattern, the protrusions 38 protrude over the edge 28 to which they are not attached. This is illustrated in FIG. 5A.

Figure 5B:
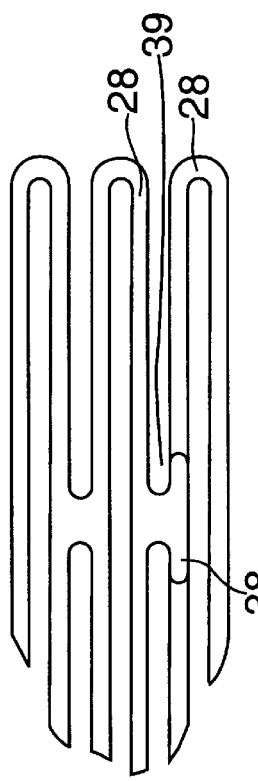

In step 16, the edges 28 are joined together by any suitable process, such as spot welding. If the protrusions 38 were made, the protrusions 38 are joined to the opposite edge 28, either by welding, adhesive or, as illustrated in FIG. 6, with a nail-like element 40. FIG. 5B illustrates the connection of the protrusion to the opposite edge 28. Since protrusion 38 is typically designed to extend the width of one loop 39, the pattern in approximately preserved. This is seen in FIG. 5B.

Alternatively, the edges 28 can be brought together and joined in the appropriate places.

Figure 4:
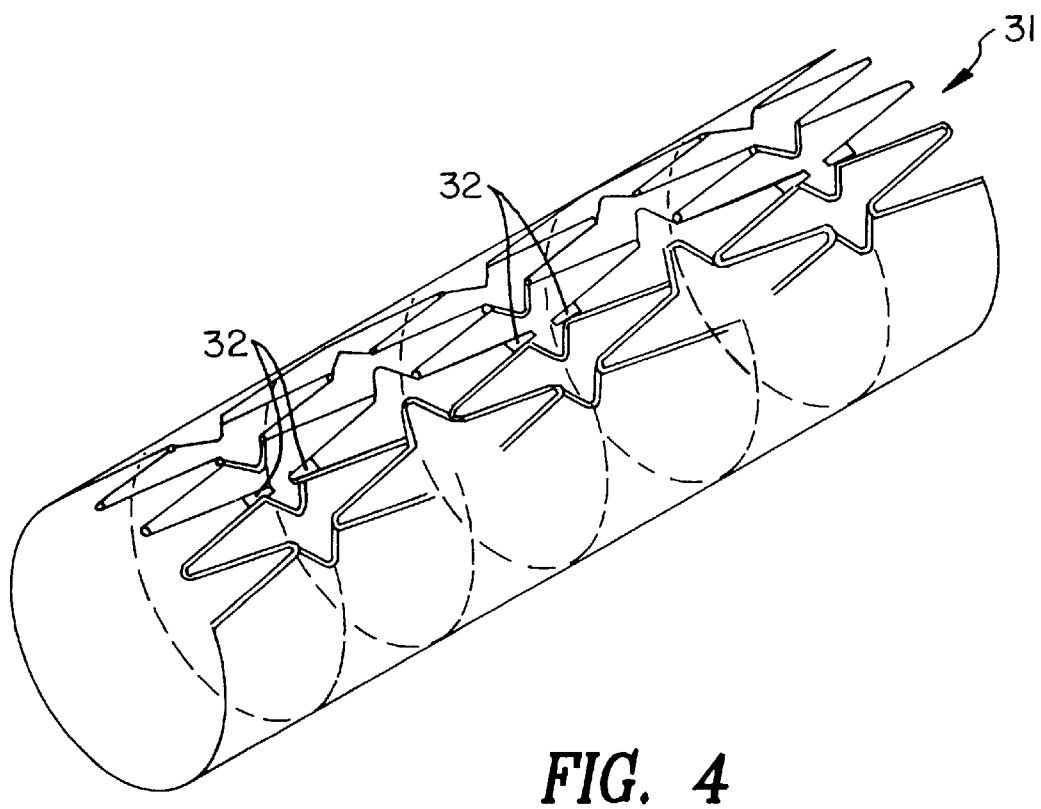
FIG. 4 is an isometric illustration of a stent formed from the method of FIG. 1.

FIG. 4 illustrates a stent 31 formed by the process of steps 10–16 for the pattern of FIG. 2A. It is noted that such a stent has connection points 32 formed by the joining of the points 30.

Finally, the stent 31 is polished to remove any excess material not properly removed by the cutting process (step 12). The polishing can be performed mechanically, by rubbing a polishing stick having diamond dust on its outside inside the stent 31. Alternatively, an electropolishing unit can be utilized.

FIG. 7 shows an alternative embodiment of the invention in which a plurality of patterns 120 are etched and cut into the sheet metal 121 as previously discussed. FIG. 8 is an enlarged view of one of the plurality of patterns 120 shown in FIG. 7.

Figure 9:
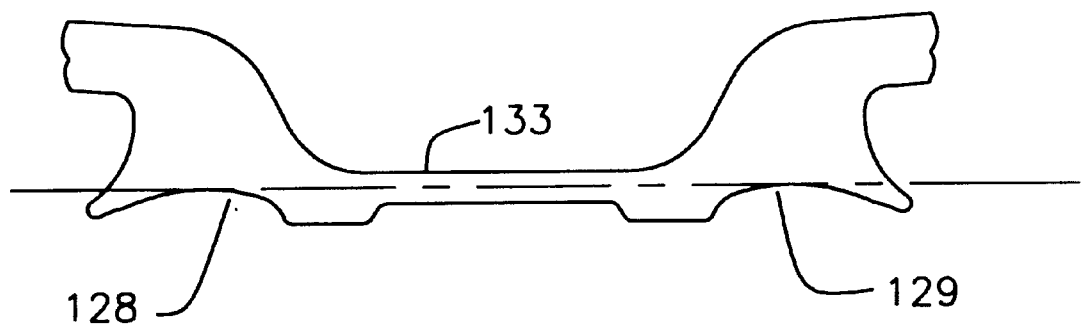
FIG. 9 shows a detailed view of a pair of engagement troughs shown in FIG. 8.
Figure 10:
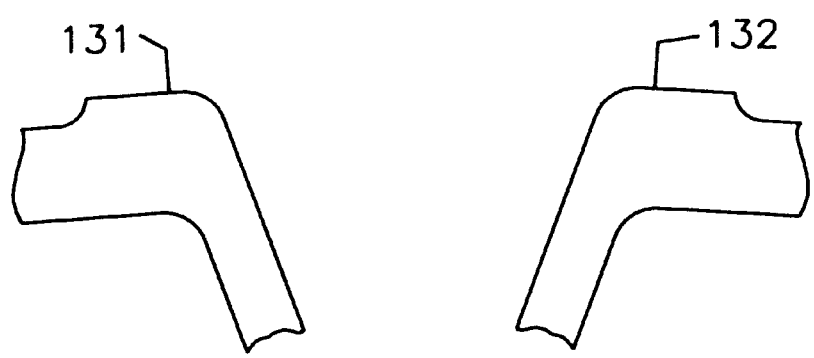
FIG. 10 shows a detailed view of a pair of engaging protrusions shown in FIG. 8.
Figure 11:
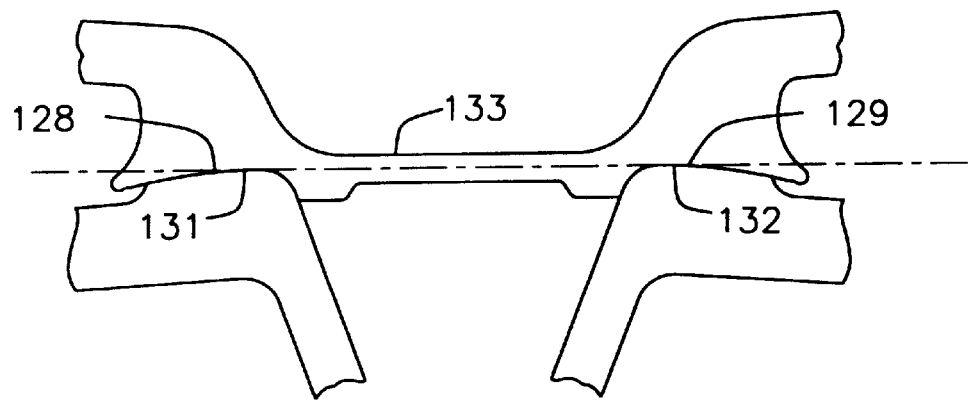
FIG. 11 shows the engagement troughs and engagement protrusions of FIGS. 9 and 10 in the engaged position.

FIG. 9 is an enlarged view of one pair 127 of the plurality of engagement troughs 128 and 129 shown in FIG. 8. FIG. 10 is an enlarged view of one pair 130 of the plurality of engagement protrusions 131 and 132 shown in FIG. 8. The sheet metal 121 and each of the patterns 120 is provided with a plurality of alignment apertures 122 and 122' adapted to receive sprockets (not shown) for precisely moving and maintaining the precise alignment of the sheet metal 121 and the patterns 120 during the various stages of manufacturing. Each pattern 120 has a first long side 123 and a second long side 124, a first short side 125, and a second short side 126. The first long side 123 is provided with a plurality of pairs 127, 127' and 127" of engagement troughs 128 and 129 (shown in greater detail in FIG. 9). Each pair 127, 127' and 127" of engagement troughs has a first engagement trough 128 and a second engagement trough 129. The second long side 124 is provided with a plurality of pairs 130, 130' and 130" of engagement protrusions (shown in greater detail in FIG. 10). Each pair 130, 130' and 130" of engagement protrusions is provided with a first engagement protrusion 131 and a second engagement protrusion 132. The pairs of engagement protrusions 130, 130' and 130" are disposed substantially opposite the pairs of engagement troughs 127, 127' and 127".

Figure 19:
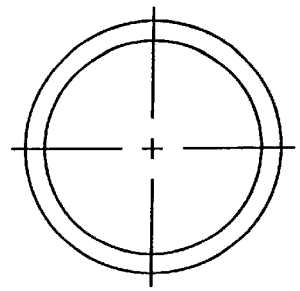
FIG. 19 is a cross-sectional view of a stent constructed in accordance with this invention.
Figure 16:
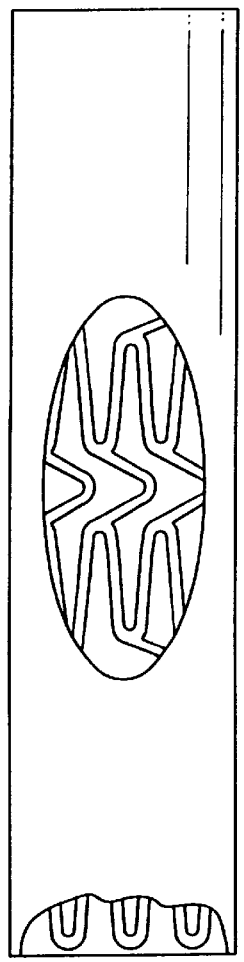
FIG. 16 shows a cell of a stent made in accordance with this invention.
Figure 17:
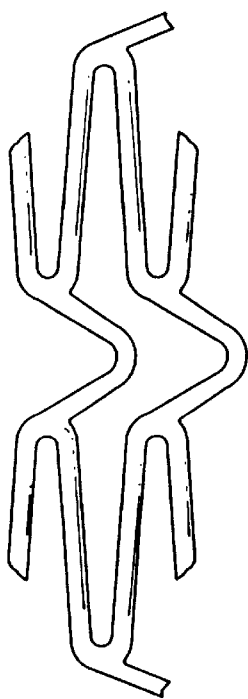
FIG. 17 is an enlarged view of the cell shown in FIG. 16.
Figure 20:
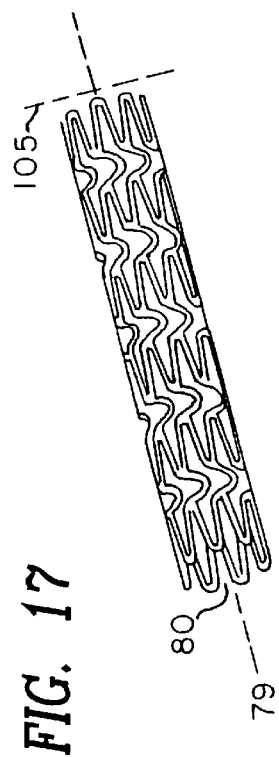
FIG. 20 is a perspective view of a stent constructed in accordance with this invention.

The engagement troughs 128 and 129 are disposed and adapted to receive and engage the engagement protrusions 131 and 132 so that the alignment of the stent is maintained when the pattern 120 is deformed and the flat sheet metal is rolled so that the first long side 123 and the second long side 124 meet each other to form a tube as shown in FIGS. 19 and 20.

A bridge 133 of material is disposed between each pair 127, 127' and 127" of engagement troughs 128 and 129. This bridge 133 imparts additional stability and facilitates alignment during manufacturing and imparts additional strength to the welds of the finished stent as discussed below.

Figure 12:
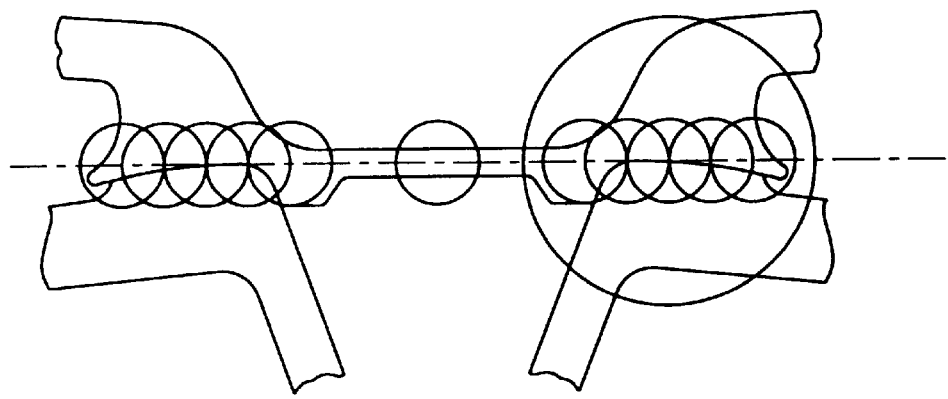
FIG. 12 shows a welding run practiced in accordance with the invention.
Figure 13:
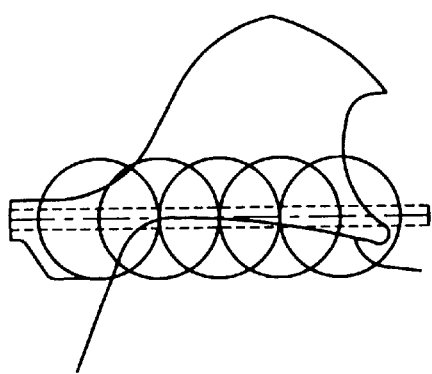
FIG. 13 is a detailed view of the welding run shown in FIG. 12.

After the sheet has been rolled into a tubular stent and the engagement troughs 128 and 129 have received the engagement protrusions 131 and 132, means (not shown) are utilized to maintain the alignment and the bridge 133 is cut to leave two substantially equal parts. The bridge 133 may be cut in a variety of ways well known to those skilled in the art, however, in a preferred embodiment, a laser is utilized. Engagement trough 128 is welded to engagement protrusion 131 and engagement trough 129 is welded to engagement protrusion 132 as shown in FIGS. 12 and 13. This may be accomplished in a variety of ways well known to those skilled in the art, however, in a preferred embodiment a plurality of spot welds are utilized. In an especially preferred embodiment, about five spot welds are used in each weld run as shown in FIGS. 12 and 13. The heat produced by the welding melts the cut bridge 133 material and the material is drawn towards the engagement trough 128 or 129 to which the material is attached and is drawn into the welded area between the engagement trough and the engagement protrusion where the additional bridge material becomes part of and imparts additional strength to the weld. The stent may then be finished as previously discussed.

FIG. 13 is an enlarged view of the welded area shown in FIG. 12. In a preferred embodiment, the weld run is offset from the point where the engagement trough and the engagement protrusion contact each other. In an especially preferred embodiment, the weld run is offset about 0.01 mm.

Figure 14:
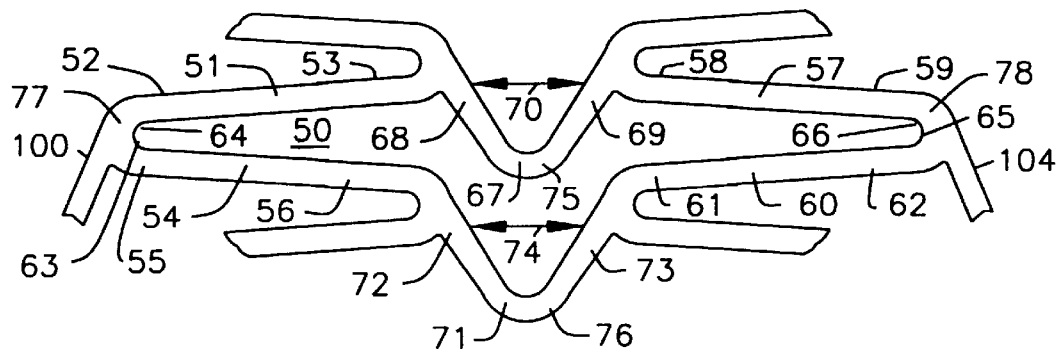
FIG. 14 is a detailed view of a cell of a stent made in accordance with this invention.

FIG. 14 is a detailed view of the pattern shown in FIG. 8. As shown in FIGS. 14 and 20, Applicants' invention can also be described as an expandable stent defining a longitudinal aperture 80 having a longitudinal axis or extension 79 and a circumferential axis or extension 105, including a plurality of flexible connected cells 50 with each of the flexible cells 50 having a first longitudinal end 77 and a second longitudinal end 78. Each cell 50 also is provided with a first longitudinal apex 100 disposed at the first longitudinal end 77 and a second longitudinal apex 104 disposed at the second longitudinal end 78. Each cell 50 also includes a first member 51 having a longitudinal component having a first end 52 and a second end 53; a second member 54 having a longitudinal component having a first end 55 and a second end 56; a third member 57 having a longitudinal component having a first end 58 and a second end 59; and a fourth member 60 having a longitudinal component having a first end 61 and a second end 62. The stent also includes a first loop 63 defining a first angle 64 disposed between the first end 52 of the first member 51 and the first end 55 of the second member 54. A second loop 65 defining a second angle 66 is disposed between the second end 59 of the third member 57 and the second end 62 of the fourth member 60 and is disposed generally opposite to the first loop 63. A first flexible compensating member or flexible link 67 having a first end 68 and a second end 69 is disposed between the first member 51 and the third member 57 with the first end 68 of the first flexible compensating member or flexible link 67 communicating with the second end 53 of the first member 51 and the second end 69 of the first flexible compensating member or flexible link 67 communicating with the first end 58 of the third member 57. The first end 68 and the second end 69 are disposed a variable longitudinal distance 70 from each other. A second flexible compensating member 71 having a first end 72 and a second end 73 is disposed between the second member 54 and the fourth member 60. The first end 72 of the second flexible compensating member or flexible link 71 communicates with the second end 56 of the second member 54 and the second end 73 of the second flexible compensating member or flexible link 71 communicates with the first end 61 of the fourth member 60. The first end 72 and the second end 73 are disposed a variable longitudinal distance 74 from each other. In a preferred embodiment, the first and second flexible compensating member or flexible links 67 and 71 are arcuate. The first and second flexible compensating member or flexible links 67 and 71 are differentially extendable or compressible when the stent is bent in a curved direction away from the longitudinal axis 79 of the aperture 80. (Shown in FIG. 20.) The first member 51, second member 54, third member 57, and fourth member 60 and the first loop 63 and the second loop 65 and the first flexible compensating member or flexible link 67 and the second flexible compensating member or flexible link 71 are disposed so that as the stent is expanded the distance between the first flexible compensating member or flexible link 67 and the second flexible compensating member or flexible link 71 increases and the longitudinal component of the first member 51, second member 54, third member 57 and fourth member 60 decreases while the first loop 63 and the second loop 65 remain generally opposite to one another, the ends 68 and 69 of the first flexible compensating member or flexible link 67 and the ends 72 and 73 of the second flexible compensating member or flexible link 71 open so as to increase the variable longitudinal distance 70 between the first end 68 and the second end 69 of the first flexible compensating member or flexible link 67 and so as to increase the variable longitudinal distance 74 between the first end 72 and the second end 73 of the second flexible compensating member or flexible link 71. This compensates for the decreasing of the longitudinal component of the first member 51, second member 54, third member 57, and fourth member 60 and substantially lessens the foreshortening of the stent upon its expansion. Upon expansion, the first flexible compensating member 67 and the second flexible compensating member 71 impart support to the lumen being treated.

Figure 15:
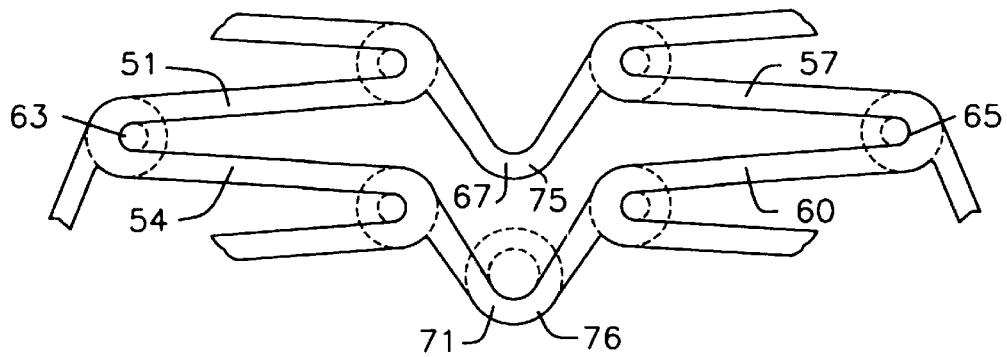
FIG. 15 is a detailed view of a cell made in accordance with this invention.
Figure 18:
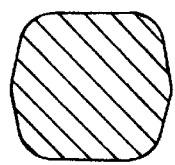
FIG. 18 is a cross-sectional view of a longitudinal member of a stent constructed in accordance with this invention.

FIG. 15 shows the dimensions of an especially preferred embodiment of this invention. The deflection points, i.e., the first and second loops 63 and 65 and the first and second compensating members 67 and 71, are made wider than the first, second, third, and fourth members 51, 54, 57 and 60 so that the force of the deflection is distributed over a wider area upon the expansion of the stent. The deflection points can be made wider than the first, second, third and fourth members in differing amounts so that the deflection will occur in the narrower areas first due to the decreased resistance. In a preferred embodiment, the first and second compensating members are wider than the first, second, third and fourth members and the first and second loops are wider than the first and second compensating members. One of the advantages of sizing the first and second loops so that they are wider than the first and second compensating members is that the stent will substantially compensate for foreshortening as the stent is expanded. In the embodiment shown in FIG. 15, the first, second, third and fourth members 51, 54, 57 and 60 have a width of about 0.1 mm. The first and second loops 63 and 65 have a width of about 0.14 mm. The first and second compensating members 67 and 71 are provided with a thickened portion 75 and 76 having a width of about 0.12 mm. Thus, in this especially preferred embodiment, the first and second loops have a width that is about 40% greater and the first and second compensating members have a width that is about 20% greater than the width of the first, second, third and fourth members.

FIGS. 16 through 20 show details of a stent constructed in accordance with this invention.

Yet another advantage of Applicant's invention is shown in FIGS. 21 to 24. For the sake of clarity, the dimensions and the degree of displacement of the components of the stents shown in FIGS. 21 to 24 has been intentionally exaggerated.

Figure 21:
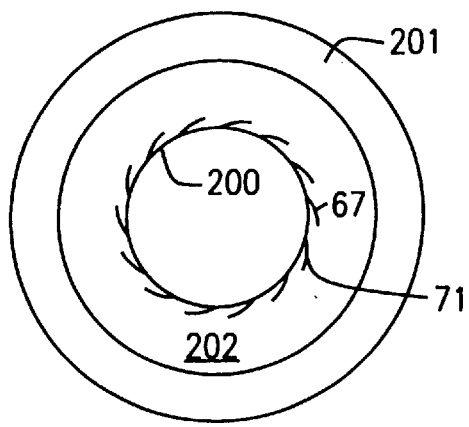
FIG. 21 is a cross-sectional front view of an unexpanded stent made in accordance with the invention.
Figure 22:
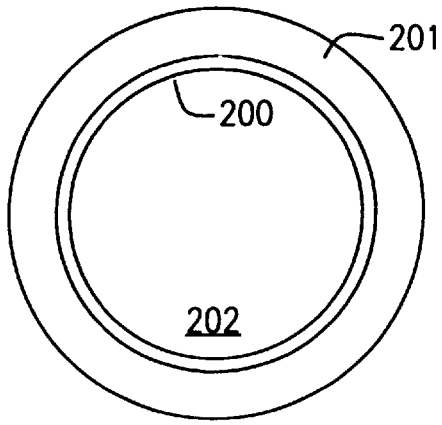
FIG. 22 is a cross-sectional front view of the stent shown in FIG. 21 after it has been expanded.

FIG. 21 is a cross-sectional front view taken along line A—A of the unexpanded stent made in accordance with applicants invention shown in FIG. 20. The unexpanded stent 200 of FIG. 21 is shown disposed in the lumen 202 of a blood vessel 201 prior to expansion. As previously discussed, this stent is made by first cutting the stent pattern into a flat piece of sheet metal and then rolling the sheet metal into a tube to form the tubular stent. As shown in FIG. 21 after rolling, the first and second flexible compensating members 67 and 71 of the unexpanded stent tend to "flare out" in a direction away from the longitudinal axis or lumen of the stent. Thus, the flexible compensating members 67 and 71 define outer diameters which are larger than the outer diameters defined by the remaining portions of the stent. FIG. 22 shows the stent of FIG. 21 after it has been expanded in the lumen and against the internal wall of the blood vessel. As shown in FIG. 22, upon expansion of the unexpanded stent toward the wall of the blood vessels, the walls of the blood vessel imparts a mechanical force to the first and second flexible compensating members 67 and 71 and the compensating members move toward the longitudinal axis or lumen of the stent until they are substantially in registry with the remaining portion of the stent. Thus, the lumen of the expanded stent is substantially circular when viewed in cross section with substantially no portion of the expanded stent projecting into the lumen or towards the longitudinal axis of the expanded stent.

Figure 23:
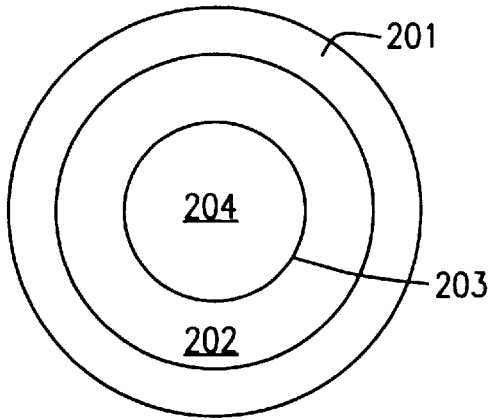
FIG. 23 is a cross-sectional front view of an unexpanded stent made by cutting a pattern in a tube.

FIG. 23 is similar to FIG. 21 except that the pattern has been cut into a tubular member using conventional methods of making stents. As shown in FIG. 23, the flexible compensating members do not flare out away from the longitudinal axis of the unexpanded stent 203. Upon the expansion of the stent shown in FIG. 23 toward the walls of the blood vessel 201, the flexible compensating members 67' and 71' tend to "flare in" and project into the lumen 204 of the expanded stent 203.

Figure 24:
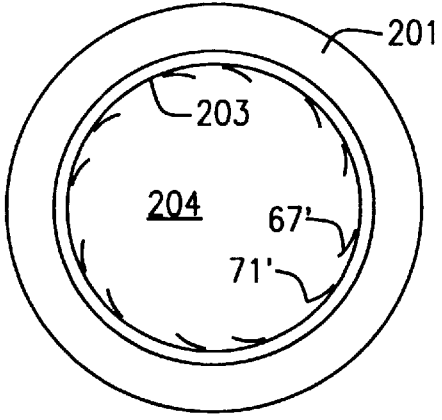
FIG. 24 is a cross-sectional front view of the stent shown in FIG. 23 after expansion.

FIG. 24 shows the stent 203 of FIG. 23 after it has been expanded in a lumen 204 of a blood vessel 201. The flexible compensating members 67' and 71' are not in registry with the remaining portions of the stent and define a diameter smaller than the diameter of remaining portions of the stent. These projections into the lumen of the stent create turbulence in a fluid flowing through the longitudinal axis of the expanded stent and could result in clot formation.

Applicant's invention is also directed to an apparatus for fabricating a stent, comprising a platform, a mandrel, and means for deforming a sheet of metal around the mandrel.

The platform is adapted to receive a flat sheet of metal to be formed into a stent. In a preferred embodiment, the flat sheet of metal is provided with a first end, a second end defining a longitudinal axis, a first major surface, a second major surface, a first long side, a second long side, with the first and said second long sides substantially parallel to the longitudinal axis of the sheet. The mandrel has a substantially cylindrical external surface and a first end and a second end defining a longitudinal axis. The mandrel is sized to have a cross-sectional diameter substantially equal to or less than the internal diameter of a stent to be fabricated. A means for securing the mandrel against a major surface of the flat sheet of metal is provided. A means for deforming the flat sheet of metal around the external surface of the mandrel is also provided to deform the flat sheet of metal into a substantially tubular shape that substantially conforms to the external surface of the mandrel. In a preferred embodiment, the means for deforming the sheet is adapted so that the first long side and the second long side remain substantially parallel to each other when the flat sheet of metal is deformed into a tubular shape. A means, e.g., a welding apparatus, laser, adhesive, or screw secures the first long side of the sheet to the second long side of the sheet.

In operation of a preferred embodiment a plurality of stent patterns are cut or etched into a flat piece of metal. Each of the patterns has a first long side and a second long side, with the first long side provided with a plurality of pairs of engagement points and second long side provided with a plurality of pairs of engagement points. The plurality of pairs of engagement points are disposed substantially opposite each other and are sized and disposed to communicate when the pattern is deformed and rolled into a tubular shape. Each pair of the first long side engagement points is provided with a bridge disposed between each first long side engagement point comprising the pair, the bridge having a width that is less than the width of the other portions of the stent.

A mandrel is disposed between the first and second long sides of the sheet. The mandrel has a substantially cylindrical external surface and a longitudinal axis substantially parallel to the first long side and the second long sides. The pattern is deformed into a tubular shape so that the first long side pairs of engagement points contact the second long side pairs of engagement points.

The bridge is cut and each of the engagement points is attached to the engagement point with which it is in contact to form the expandable stent.

FIGS. 25 to 28 show a preferred embodiment of an apparatus for fabricating and a stent constructed in accordance with Applicants' invention. The apparatus comprises a laser housing 300, a laser 301, a movable table 302, and a plurality of stent folders 303 disposed on the table. The laser 301 is disposed within and selectively movable within the housing 300. The movable table 302 has a first end 304 and a second end 305 and is adapted for selective movement into and out of the laser housing 300. The table 302 is adapted so that when the first end 304 of the table 302 is disposed within the laser housing 300 the second end of the table 305 is disposed outside of said housing 300 and when said second end 305 of the table 302 is disposed within the laser housing 300 the first end 304 of the table 302 is disposed outside of the laser housing 300.

Figure 26:
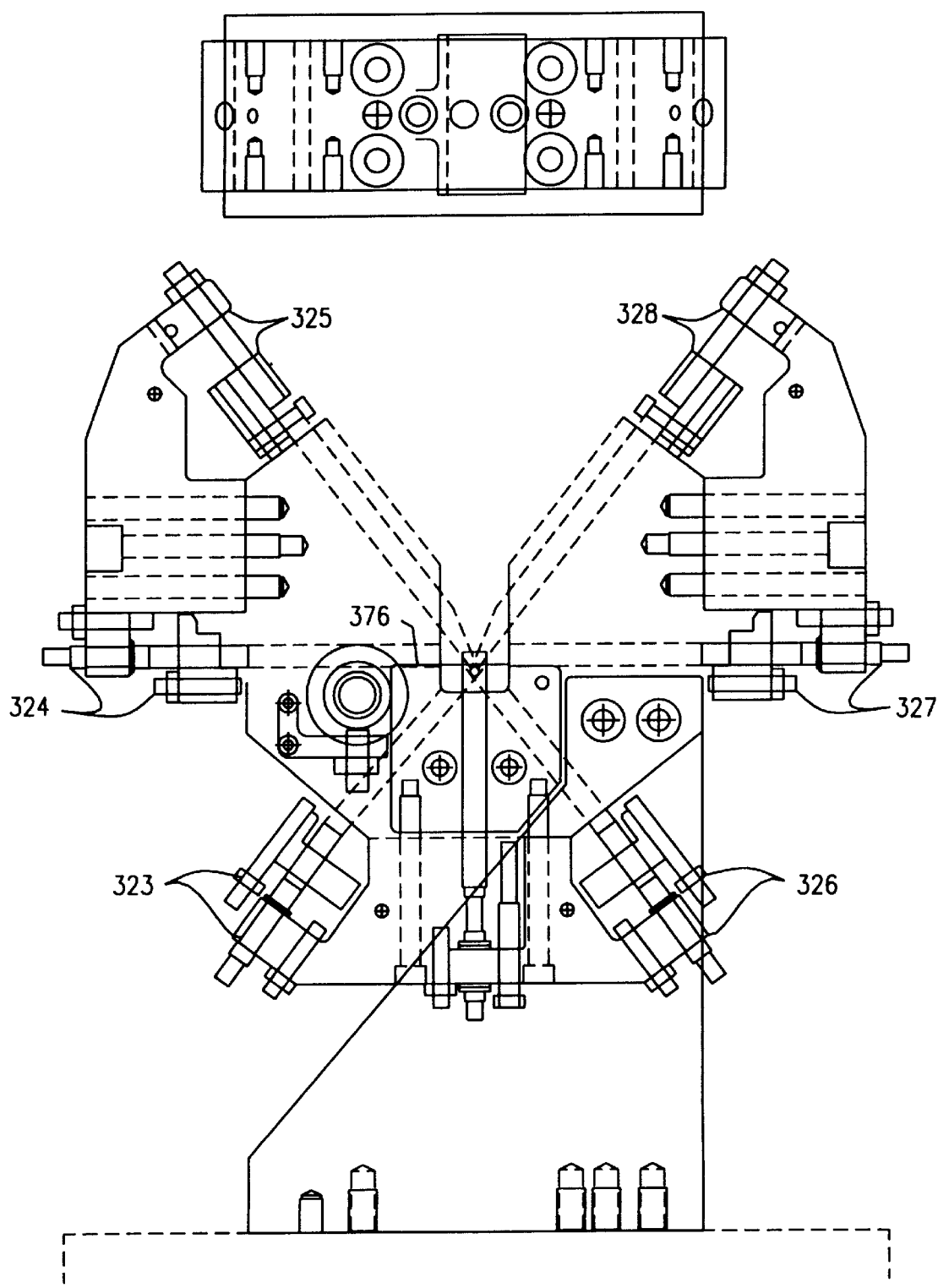
FIG. 26 shows an apparatus for constructing a stent made in accordance with the invention.
Figure 27:
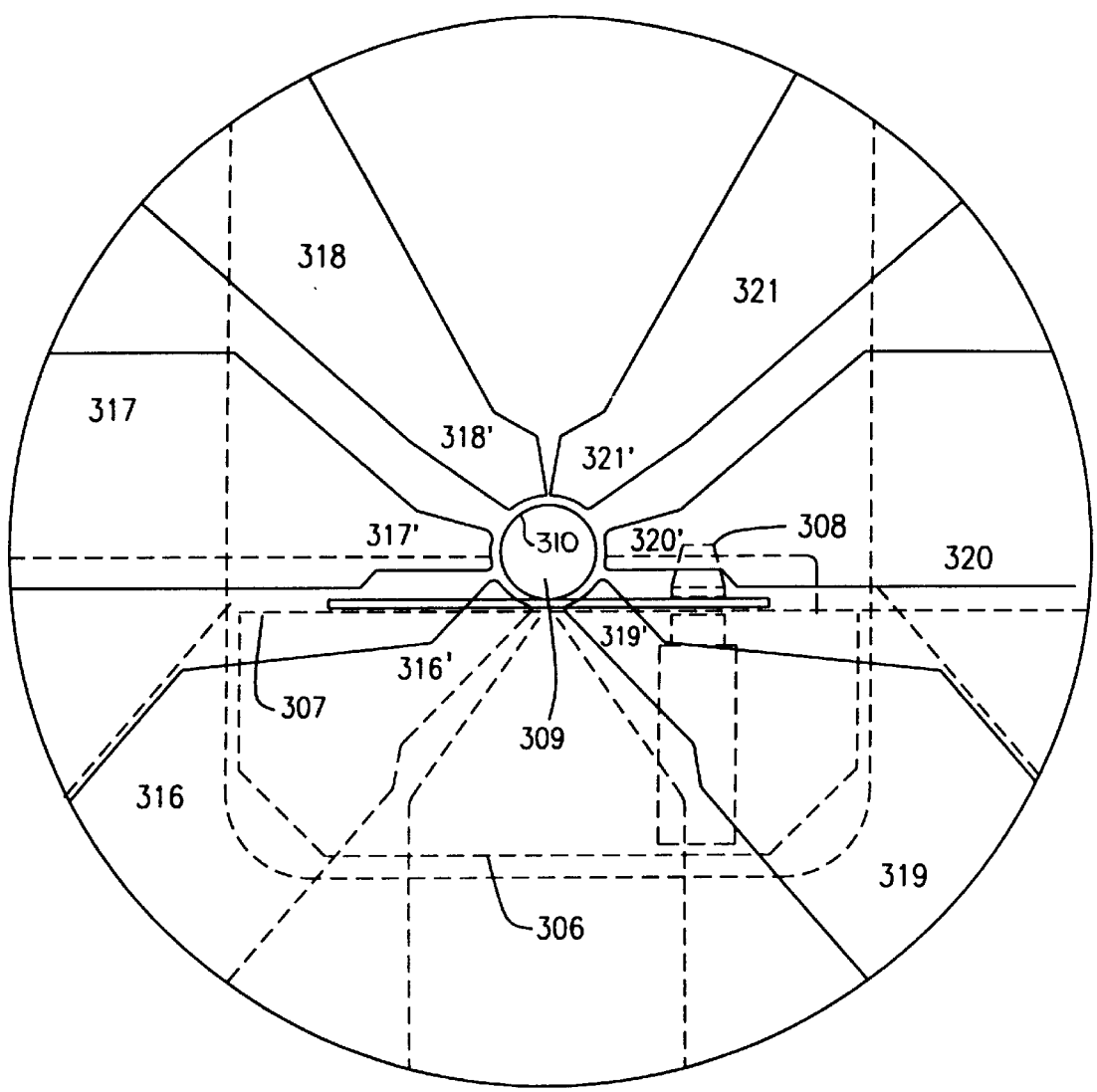
FIG. 27 is an enlarged view of a portion of the apparatus shown in FIG. 26.

A plurality of stent folders 303 is disposed at the first end 304 of the table and a plurality of stent folders 303 is disposed at the second end 305 of the table 302. As shown in FIGS. 26 and 27, each of said stent folders comprises:

A base 306 having a platform 307 adapted to receive a flat sheet of metal 120 to be formed into a stent. The flat sheet of metal 120 has a longitudinal axis, a first major surface, a second major surface, a first long side, and a second long side, with the first and the second long sides substantially parallel to the longitudinal axis. The sheet is also provided with a plurality of alignment of apertures.

A plurality of alignment pins 308 project from each of the platforms. The pins 308 are sized to engage the alignment apertures 122 and align the sheet on the platform 307.

Figure 35:
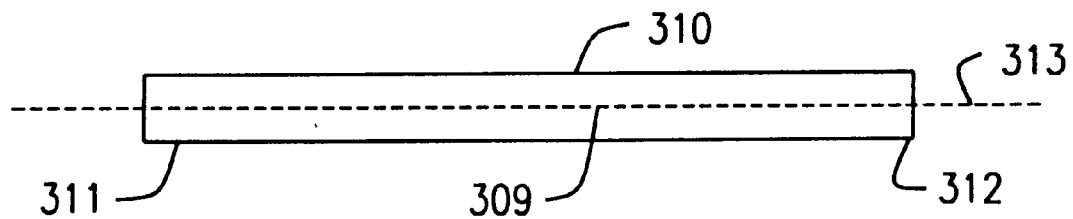
FIG. 35 shows a mandrel utilized in accordance with the invention.
Figure 36:
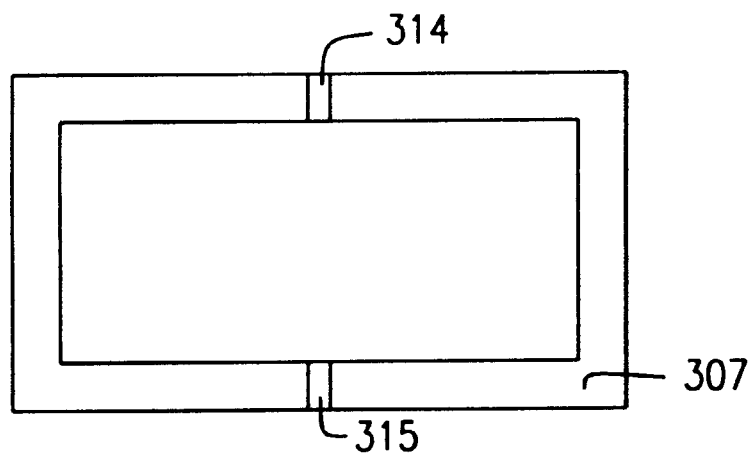
FIG. 36 shows a mandrel receiving surface made in accordance with the invention.
Figure 37:
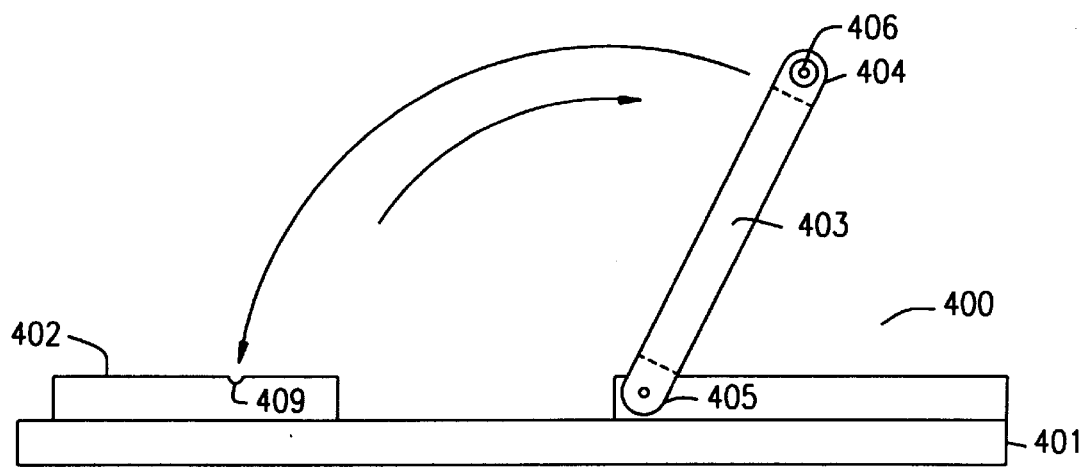
FIG. 37 shows an alternative embodiment of an apparatus constructed in accordance with the invention.
Figure 38:
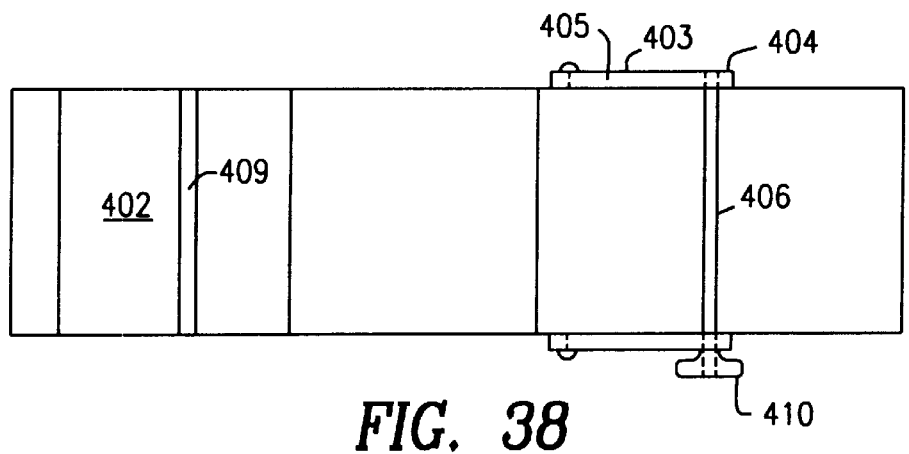
FIG. 38 is a top view of FIG. 37.

A mandrel 309 is provided having a substantially cylindrical external surface 310 and having a first end 311, a second end 312, and a longitudinal axis 313 as shown in FIGS. 35. The mandrel 309 is sized to have a cross-sectional diameter substantially equal to or less than the internal diameter of the stent to be fabricated. The platform 307 is provided with a first concave recess 314 adapted to receive the first end 311 of the mandrel and a second concave recess 315 adapted to receive the second end 312 of the mandrel 309 as shown in FIG. 36.

A hingedly connected arm 316 is adapted for movement in a first direction toward the platform 307 and in a second direction away from the platform 307 for securing the mandrel 309 against a major surface of said flat sheet of metal when it is disposed on the platform.

Each stent folder 303 is provided with a first deforming blade 316 provided with a first deforming blade tip 316'; a second deforming blade 317 provided with a second deforming blade tip 317'; a third deforming blade 318 provided with a third deforming blade tip 318'; a fourth deforming blade 319 provided with a fourth deforming blade tip 319'; a fifth deforming blade 320 provided with a fifth deforming blade tip 320'; and a sixth deforming blade 321 provided with a sixth deforming blade tip 321'. The blades are disposed around the external surface 310 of the mandrel 309 and are adapted to deform the flat sheet of metal against the external surface 310 of the mandrel 309 so that the flat sheet of metal is deformed into a substantially tubular shape substantially conforming to the external surface 310 of the mandrel 309. The deforming blades are disposed between the first end 311 and the second end 312 of the mandrel 309. Each of the deforming blades is adapted for independent and selective movement in a first direction toward the mandrel 309 and a second direction away from the mandrel so as to selectively impinge the deforming blade tips 316', 317', 318', 319', 320', and 321' against the mandrel or against a portion of the sheet disposed between the mandrel and each of the deforming blade tips. Each of the deforming blades is also adapted so that the first long side and the second long side of the sheet remain substantially parallel to each other when the sheet is deformed into the tubular shape. The third and the sixth deforming blade tips 318' and 321' are provided with a plurality of scalloped laser apertures 322 which are sized and disposed to permit the third and the sixth deforming blade tips to secure the first long side and the second long side against the external surface of the mandrel while providing the laser 301 access to predetermined portions of the first long side and the second long side in order to weld the first long side to the second long side.

A first motor 323 is connected to the first deforming blade; a second motor 324 is connected to the second deforming blade; a third motor 325 is connected to the third deforming blade; a fourth motor 326 is connected to the fourth deforming blade; a fifth motor 327 is connected to the fifth deforming blade; and a sixth motor 328 is connected to the sixth deforming blade. Each of the motors is adapted for selectively moving each of the deforming blades to which it is connected in a first direction toward the mandrel and in a second direction away from the mandrel.

A computer 329 controls the sequence which the first end of the table and the second end of the table are disposed within the laser housing; the sequence and degree to which each of the deforming blade tips impinges upon the mandrel or a portion of the sheet disposed between the mandrel and each of the deforming blade tips; and the sequence, pattern, location, and amount of energy the laser applies to each of the first and second long sides of each of the sheets disposed on each of the plurality of stent folders.

Each of the blade deforming tips has a length substantially equal to the first and the second long sides of the flat sheet of metal and in a preferred embodiment the blade tips are concave as shown in FIG. 27.

In an especially preferred embodiment, as shown in FIG. 27 the third deforming blade tip is substantially identical to the sixth deforming blade tip; the second deforming blade tip is substantially identical to the fifth deforming blade tip; and the first deforming blade tip is substantially identical to the fourth deforming blade tip.

Figure 25:
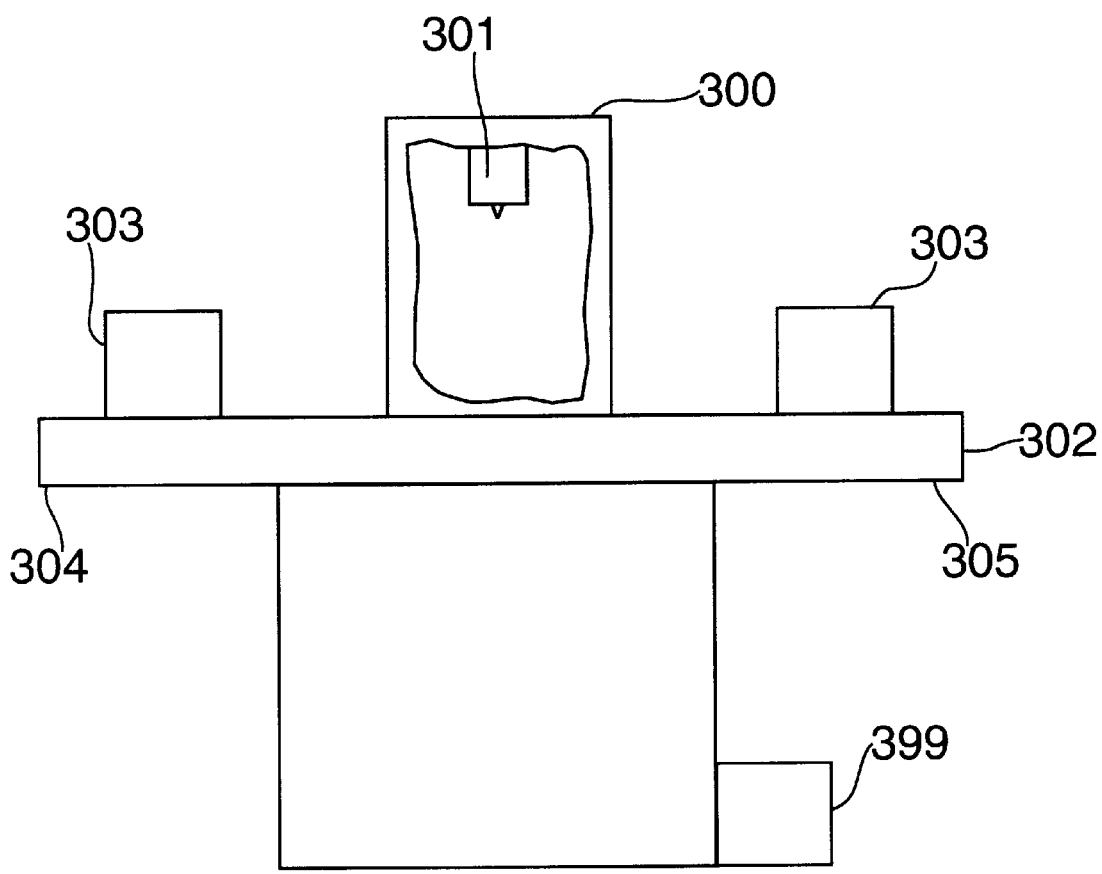
FIG. 25 shows an apparatus for constructing a stent made in accordance with the invention.
Figure 28:
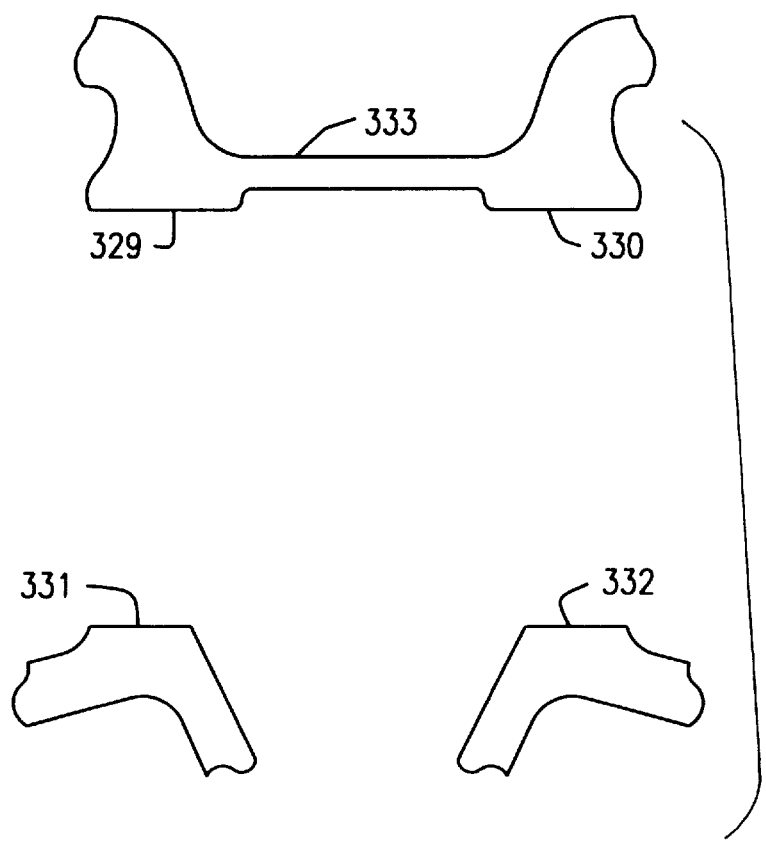
FIG. 28 shows engagement points constructed in accordance with the invention.
Figure 29:
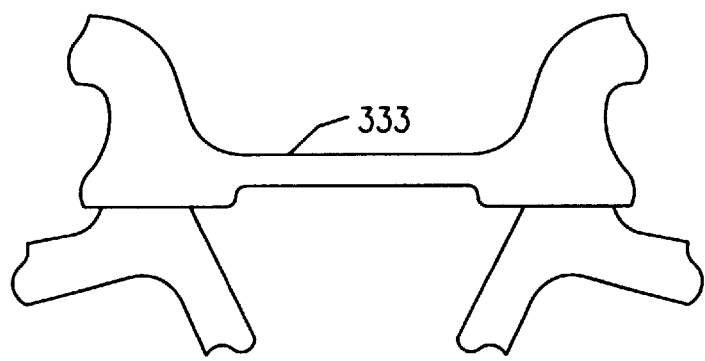
FIG. 29 show engagement points constructed in accordance with the invention.

In operation, the apparatus shown in FIGS. 25 to 27 and discussed in detail above is constructed. A plurality of stent patterns is cut into a flat piece of metal, each of the patterns having a first major surface and a second major surface, a first long side and a second long side. The first long side and the second long sides are provided with a plurality of pairs of engagement points 329, 330, 331, and 332, as shown in FIGS. 28 and 29, disposed substantially opposite each other and sized and disposed to communicate when the pattern is deformed and rolled into a tubular shape. Each pair of the first long side engagement points is provided with a bridge 333 disposed between each first long side engagement point 329 and 330 comprising the pair. Preferably, the bridge 333 has a width that is less than the width of the other portions of the stent. The sheet is also provided with a plurality of alignment apertures sized and disposed to engage the alignment pins 308 on the base 306.

The sheet is disposed on the base so that the first major surface of the sheet is in contact with the base.

Figure 30A:
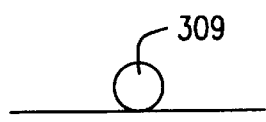
FIG. 30A to 30I shows the sequence of making a stent using the apparatus of FIGS. 25 and 26.

A mandrel 309 having a substantially cylindrical external surface 310 and a longitudinal axis 313 is disposed against the second major surface of the sheet between the first long side and the second long side of the sheet with the longitudinal axis substantially parallel to the first long side and the second long side, as shown in FIG. 30A.

Figure 30B:
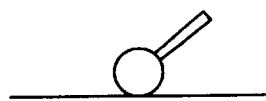

The pattern is deformed into a tubular shape so that the first long side pairs of engagement points contact the second long side pairs of engagement points, as shown in FIG. 29. The deforming step comprises the steps of:

a) actuating the sixth deforming blade motor so that the sixth deforming blade motor moves the sixth deforming blade in the first direction in an amount sufficient for the sixth deforming blade tip to contact the external surface of the mandrel so as to secure said mandrel against said sheet, as shown in FIG. 30B.

Figure 30C:
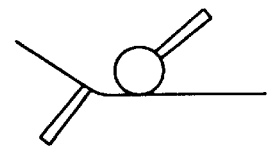

The first blade deforming motor is activated so that the first blade deforming motor moves the first deforming blade in the first direction in an amount sufficient for the first blade deforming tip to contact the first major surface of the sheet and deform the sheet against the external surface of the mandrel, as shown in FIG. 30C.

Figure 30D:
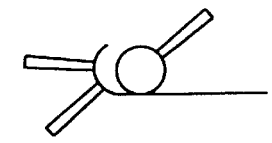

The second deforming blade motor is then activated so that the second deforming blade motor moves the second deforming blade in the first direction in an amount sufficient for the second deforming blade tip to contact the first major surface of the sheet and deform the sheet against the external surface of the mandrel, as shown in FIG. 30D.

Figure 30E:
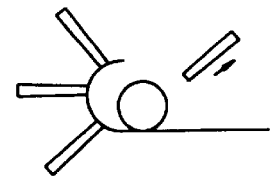

The third deforming blade motor is then activated so that the third deforming blade motor moves the second deforming blade in the first direction in an amount sufficient for the third deforming blade tip to contact the first major surface of the sheet and deform the sheet against the external surface of the mandrel while actuating the sixth deforming blade motor so that the sixth deforming blade moves in the second direction away from said mandrel, as shown in FIG. 30E.

Figure 30F:
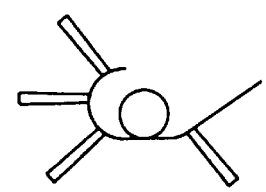

The fourth deforming blade motor is then activated so that the fourth deforming blade motor moves the fourth deforming blade tip in the first direction in an amount sufficient for the fourth deforming blade tip to contact the first major surface of the sheet and deform the sheet against the external surface of the mandrel, as shown in FIG. 30F.

Figure 30G:
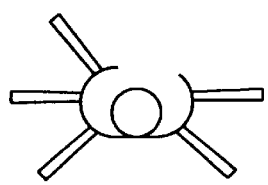

The fifth deforming blade motor is then activated so that the fifth deforming blade motor moves the fifth deforming blade in the first direction in an amount sufficient for the fifth deforming blade tip to contact the first major surface of the sheet and deform the sheet against the external surface of the mandrel, as shown in FIG. 30G.

Figure 30H:
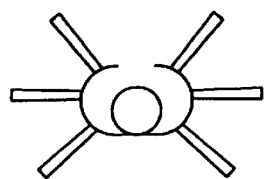

The sixth deforming blade motor is then activated so that the sixth deforming blade motor moves the sixth deforming blade in said first direction in an amount sufficient for said sixth deforming blade tip to contact the first major surface of the sheet and deform the sheet against the external surface of the mandrel, as shown in FIG. 30H.

Figure 30I:
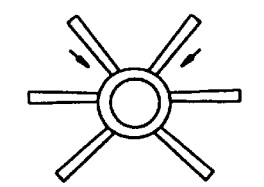

The third and sixth deforming blade motors are then simultaneously activated so that the third and sixth deforming blade motors move the third and sixth deforming blades in the first direction in an amount sufficient for the third and sixth deforming blade tips to contact the first major surface of the sheet and deform the sheet against the external surface of the mandrel as shown in FIG. 30I.

The laser is used to cut the bridge. The laser is then used to weld each of the engagement points to the engagement point with which it is in contact to form the expandable stent.

In a preferred embodiment, the bridge has a width that is about 25% to about 50% of the width of the other portions of said stent and in an especially preferred embodiment the bridge has a width of about 40 microns.

The engagement points, as shown in FIGS. 28 and 29 are sized and adapted to move in an amount sufficient so as to reduce the likelihood of material stress occurring during welding heating and cooling cycles.

Figure 31:
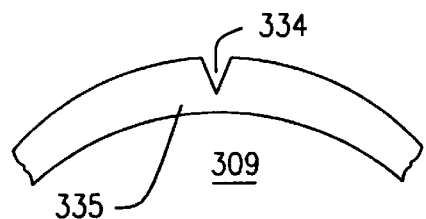
FIG. 31 shows details of a v-shaped notch and gap formed in accordance with the invention.
Figure 32:
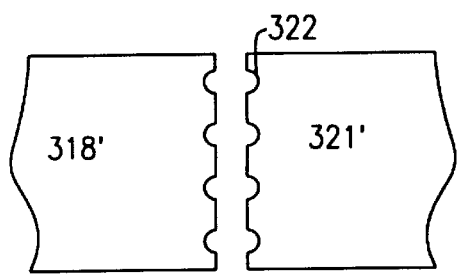
FIG. 32 shows details of two blade deforming tips made in accordance with the invention.

A V-shaped notch 334 may be formed between the first long side and the second long side when the stent is deformed to provide for a stronger weld, as shown in FIG. 31. In addition, as shown in FIG. 31 a gap 335 may be provided between the engagement points and the external surface of the mandrel 309 during the deforming step. This gap 335 provides a greater area for weld material, thus, strengthening the weld and reducing heat dissipation through the mandrel during welding, thus, reducing the amount of energy that must be put into the weld.

Figure 33:
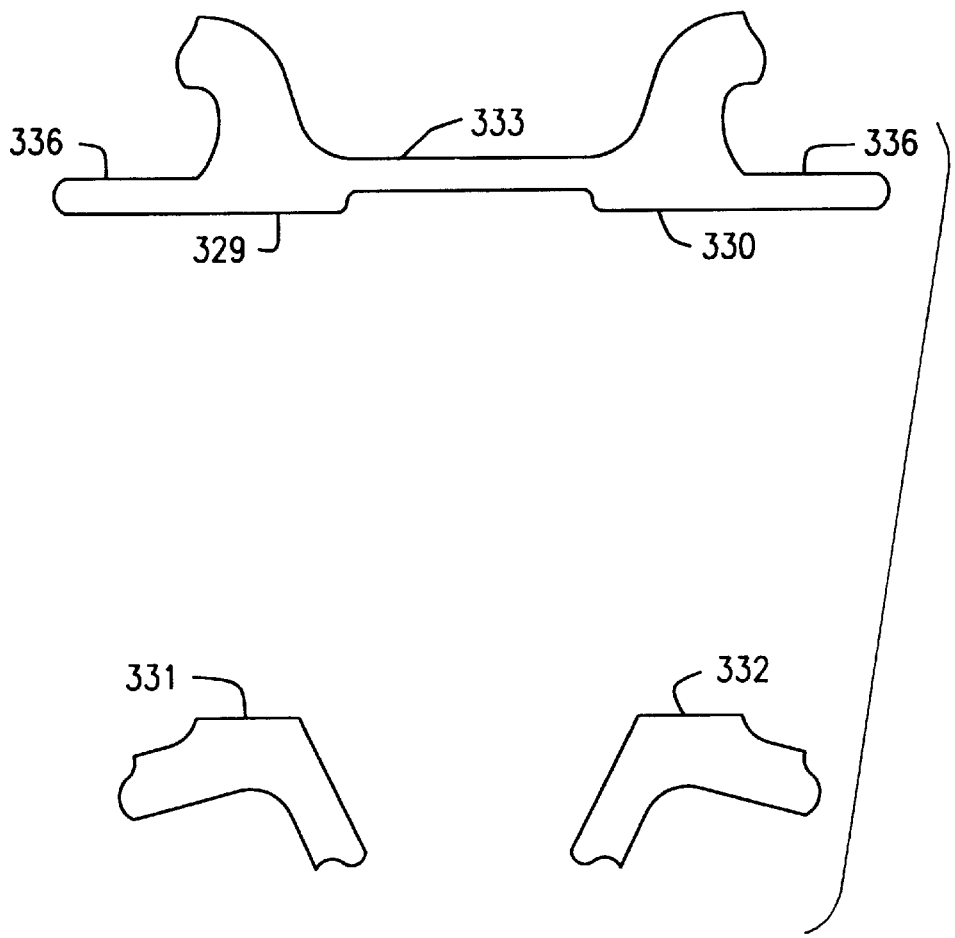
FIG. 33 shows an alternative embodiment of engagement of engagement points constructed in accordance with the invention.
Figure 34:
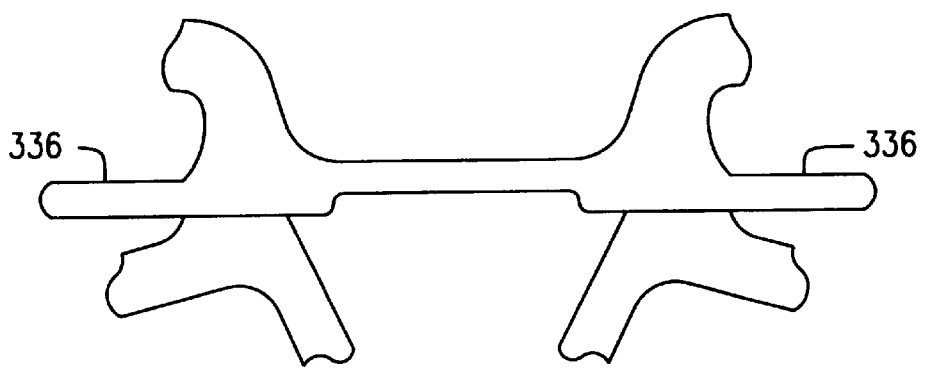
FIG. 34 shows an alternative embodiment of engagement points constructed in accordance with the invention.

Additional weld fill material 336 may be provided on the side of each of the engagement points substantially opposite the bridge, as shown in FIGS. 33 and 34. The weld fill material is sized and disposed so as to permit the additional weld fill material to be drawn into the weld point during welding.

After the stent has been deformed and the engagement points have contacted each other, the bridge is cut using the laser. The first side and long sides are then connected using the laser to form a weld that is preferably wider than the other portions of the stent. In an especially preferred embodiment, the weld is about 20% wider than the other portions of the stent and has a width of about 140 microns.

The weld is preferably run from outside-to-in. A plurality of welding runs is preferably used and in an especially preferred embodiment two weld-runs are utilized. The weld-run may be offset from the point where the engagement points contact each other and in a preferred embodiment is offset about 0.01 mm from the point where said engagement points contact each other.

The weld may be a spot weld, a plurality of spot welds, and in a preferred embodiment, the weld comprises 5 spot welds.

In a preferred embodiment, the pattern is cut into the sheet using multiple-up-etching and comprises the step of inspecting both sides of the sheet after etching and before the sheet is disposed on the base. In an especially preferred embodiment the inspection step is carried out using an automated optical inspection apparatus.

In an especially preferred embodiment, the stent patterns are adapted so that upon the expansion of the stent against the internal wall of a vessel substantially no portion of the stent projects into the longitudinal lumen of the stent. The stent may be finished by electropolishing.

FIGS. 37 to 40 show another embodiment of an apparatus for fabricating a stent constructed in accordance with the invention.

A base 401 is provided with a sheet receiving area 402 and is adapted to receive a flat sheet of metal to be formed into a stent. The sheet receiving area 402 is also provided with a mandrel receiving groove 409. In a preferred embodiment, the flat piece of metal has a longitudinal axis, a first major surface, a second major surface, a first long side, and a second long side, with the first and the second long sides substantially parallel to the longitudinal axis. An arm 403 having a first end 404 and a second end 405 is provided.

The first end 404 of the arm is adapted to selectively retain a mandrel 406 having a substantially cylindrical external surface. The second end of the arm 405 is hingedly connected to the base 401 and is adapted for movement in a first direction toward the base 401 and in a second direction away from the base 401 to secure the mandrel against a major surface of the flat sheet of metal. The mandrel 406 is sized to have a cross-sectional diameter substantially equal to or less than the internal cross-sectional diameter of the stent to be fabricated.

Figure 39:
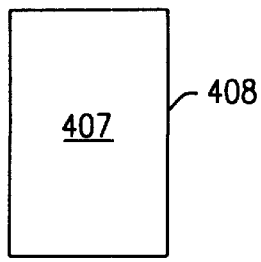
FIG. 39 shows a means for deforming a stent made in accordance with the embodiment shown in FIGS. 37 and 38.
Figure 40:
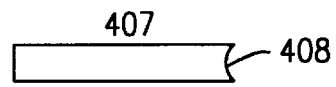
FIG. 40 is a side view of the deforming means shown in FIG. 39.
Figure 41:
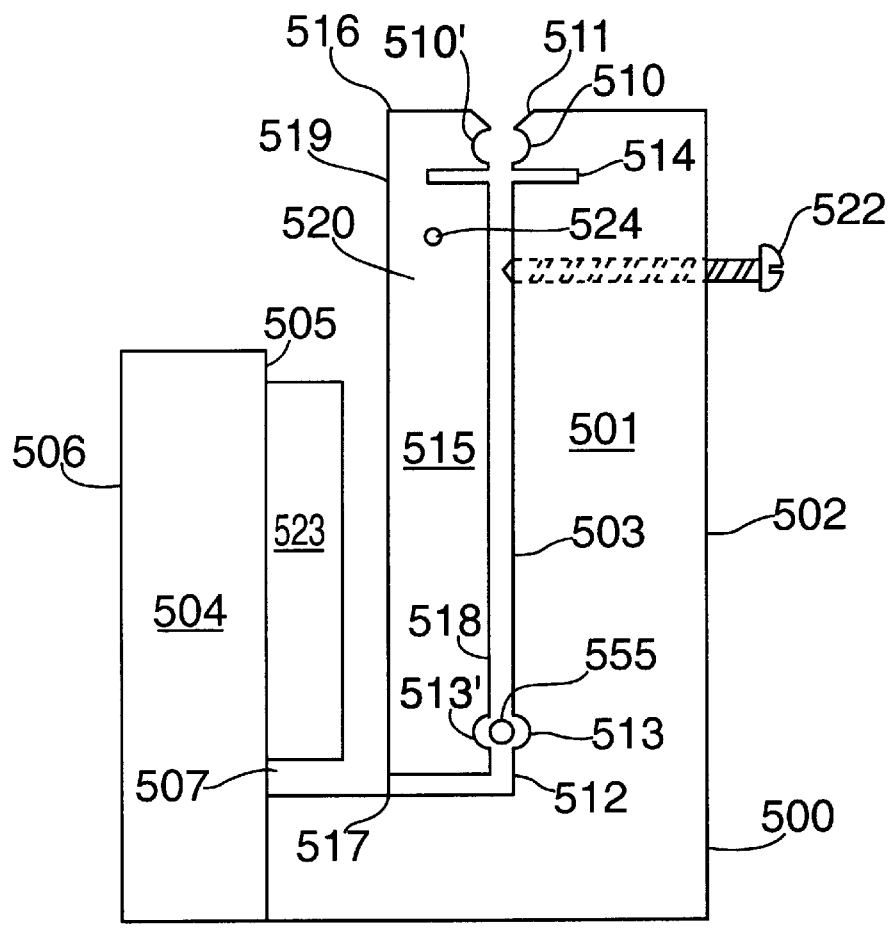
FIG. 41 shows a stent aligning and welding jig constructed in accordance with the invention.

A means 407 is provided for deforming the flat piece of metal against and around the external surface of the mandrel so that the flat sheet of metal is deformed into a substantially tubular shape conforming to the external surface of the mandrel with the first long side and the second long side substantially parallel to each other. FIG. 39 shows one embodiment wherein the means 407 for deforming is a member provided with a deforming tip 408 having a length substantially equal to the length of the first and second long sides of the sheet metal. In a preferred embodiment, the deforming tip is concave, as shown in FIG. 40.

In operation, a sheet is placed on the sheet receiving area 402. A mandrel 406 is disposed in the first end 404 of the arm 403 and the arm 403 is moved in the first direction so that the mandrel is in contact with the sheet. The deforming means is then used to deform the sheet around the mandrel a previously discussed. The arm is then moved in the second direction and the mandrel with the sheet wrapped around it is removed from the first end 404 of the arm 403. The first and second long sides are then connected as previously discussed to form the stent. In a preferred embodiment, the mandrel with the sheet wrapped around it is transferred to the stent aligning and welding jig shown in FIGS. 41 to 45.

The stent aligning and welding jig shown in FIGS. 41 to 45 comprises a base 500 having a first end and a second end provided with a first wall 501 having a first end and a second end and a first major surface 502 and a second major surface 503 and a second wall 504 having a first end and a second end and a first major surface 505 and a second major surface 506. The second major surface 503 of the first wall 501 and the first major surface 505 of the second wall 504 define a longitudinal U-shaped channel 507 having a longitudinal axis in the base 500. The first wall 501 is provided with a plurality of slots 508 defining a plurality of first clamping portions 509 having a top end 511 and a bottom end 512 and a first major surface 502 and a second major surface 503. Each of the first clamping portions 509 is provided with a first concave channel 510 disposed at the top end 511 of the second major surface 503 of the first clamping portion 509 and a second concave channel 513 disposed at the bottom end 512 of the second major surface 503 of the first clamping portion 509. The first and the second concave channels 510 and 513 are substantially parallel to the longitudinal axis of the U-shaped channel. The second major surface 503 of each of the plurality of first clamping portions is also provided with a compensation slit 514 disposed between the first concave channel 510 and the second concave channel 513 substantially parallel to the longitudinal axis of the U-shaped channel 507.

A plurality of second clamping portions 515 is disposed in the U-shaped channel 507 between the second major surface 503 of the first wall 501 and the first major surface 505 of the second wall 504. Each of the second clamping portions 515 is disposed in registry with one of the first clamping portions 509. Each of the second clamping portions 515 has a top end 516, a bottom end 517, a first major surface 518, a second major surface 519, a first minor surface disposed at the top end, a second minor surface disposed at the bottom end, a third minor surface disposed between the top end and the bottom end, and a fourth minor surface disposed opposite the third minor surface between the top end 516 and the bottom end 517. Each of the second clamping portions 515 is provided with a first concave channel 521 disposed at the top end 516 of the first major surface 518 of the second clamping portion 515 and a second concave channel 522 disposed at the bottom end 517 of the first major surface 518 of the second clamping portion 515. The first and the second concave channels 521 and 522 are substantially parallel to the longitudinal axis of the U-shaped channel.

A biasing means 523 is disposed between the first major surface 505 of the second wall 504 and the second major surface 503 of each of the of second clamping portions 509 for biasing the first major surface of each of the second clamping portions against the second major surface of each of the first clamping portions which are in registry with each other.

A first mandrel support lever positioning pin 524 projects from the third minor surface 520 and a second mandrel support lever positioning pin 521 projects from the fourth minor surface of each of the second clamping portions 515. The mandrel support lever positioning pins 524 and 521 are substantially parallel to the longitudinal axis of the U-shaped channel.

A biasing control means 522 selectively controls the distance between the second major surface 503 of each of the first clamping portions 509 and the first major surface 518 of each of the second clamping portions 515.

A retaining mandrel 523 is disposed in the second concave channel 513 of the first wall 501 and the second concave channel 522 in each of the second clamping portions 515.

Figure 42:
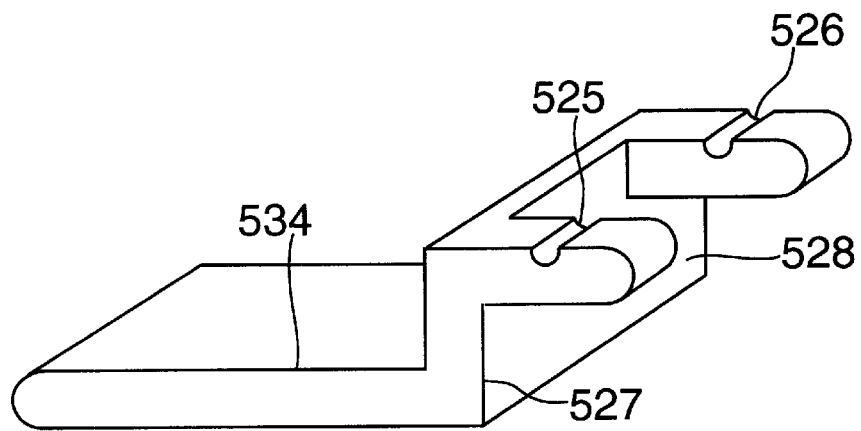
FIG. 42 shows a mandrel support lever.
Figure 43:
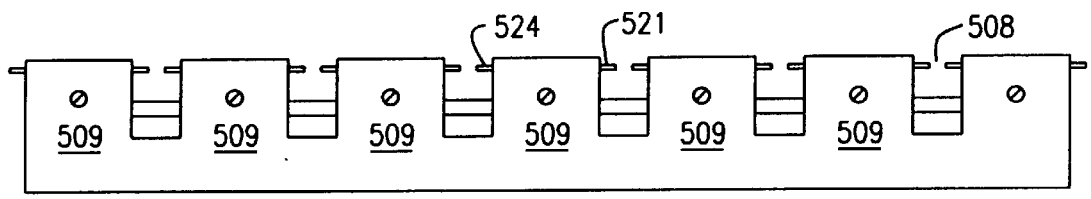
FIG. 43 is a front view of the jig shown in FIG. 41.
Figure 44:
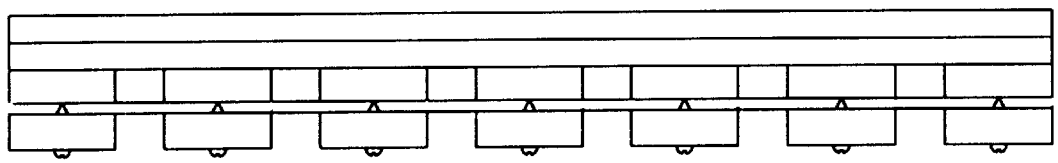
FIG. 44 is a top view of the jig shown in FIG. 43.
Figure 45:
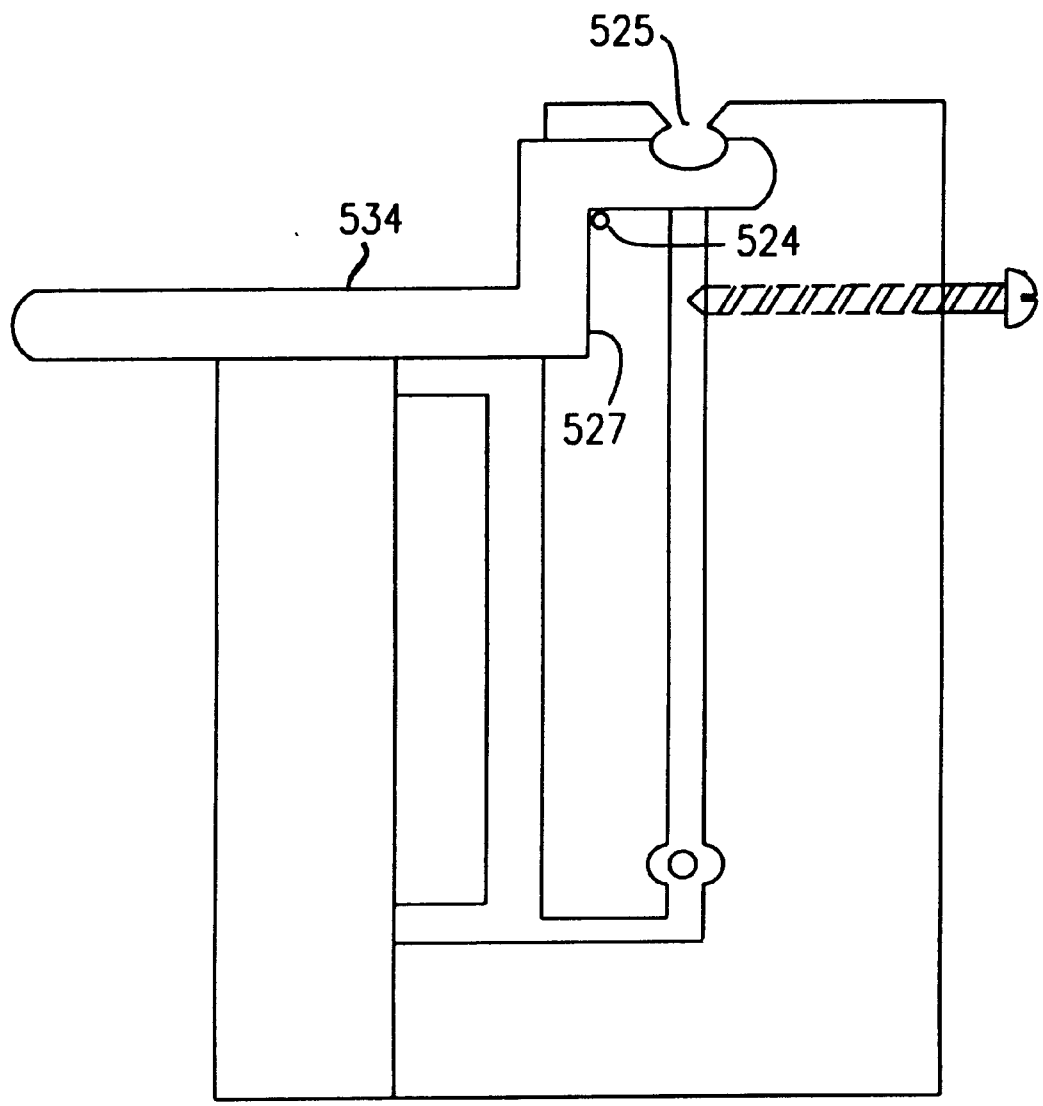
FIG. 45 shows the mandrel support lever of FIG. 42 disposed on the jig of FIG. 41.

A mandrel support lever 534, as shown in FIG. 42, supports the stent during the alignment of the first long side of the sheet with the second long side of the sheet. The lever 534 is provided with a first mandrel support notch 525 for supporting the first end of the mandrel and a second mandrel support notch 526 for supporting the second end of the mandrel. A first mandrel support lever positioning pin engagement surface 527 engages the first mandrel support lever positioning pin 524 and a second mandrel support lever positioning pin engagement surface 528 engages the second mandrel support lever positioning pin when the mandrel support lever is disposed on the second wall.

It will be appreciated that various elastic materials well known to those skilled in the art as suitable for this purpose may be utilized, e.g., a spring, however, in an especially preferred embodiment, the elastic material is rubber.

In a preferred embodiment the biasing control means 522 is a threaded screw disposed in each of the first clamping portions 509 with each of the screws 522 communicating with the first major surface 502 and the second major surface 503 of each of the first clamping portions 509. The screws 522 are selectively movable in a direction toward and away from the first major surface 518 of the second clamping portion 515 to selectively move the second clamping portion 515 in a direction toward and away from the first clamping portions 509 to selectively vary the distance between the second major surface 503 of each of the first clamping portions 509 and the first major surface 518 of each of the second clamping portions 515.

In operation, the mandrel with the sheet wrapped around it is secured in the first concave channels 510 and 521. The biasing control means 522, e.g., a screw, is adjusted to secure the mandrel in the first concave channels while permitting the first and second long sides of the sheet to be adjusted so that the contact points are aligned as desired. In a preferred embodiment, the mandrel support lever shown in FIG. 42, is utilized to support the mandrel during the alignment operation. A shown in FIG. 45, the first mandrel support notch supports the first end of the mandrel and the second mandrel support notch supports the second end of the mandrel. The first mandrel support lever positioning pin surface engages the first mandrel support lever positioning pin and the second mandrel support lever positioning pin surface engages the second mandrel support positioning pin so as to align the mandrel support lever when it is supporting the mandrel.

Figure 47:
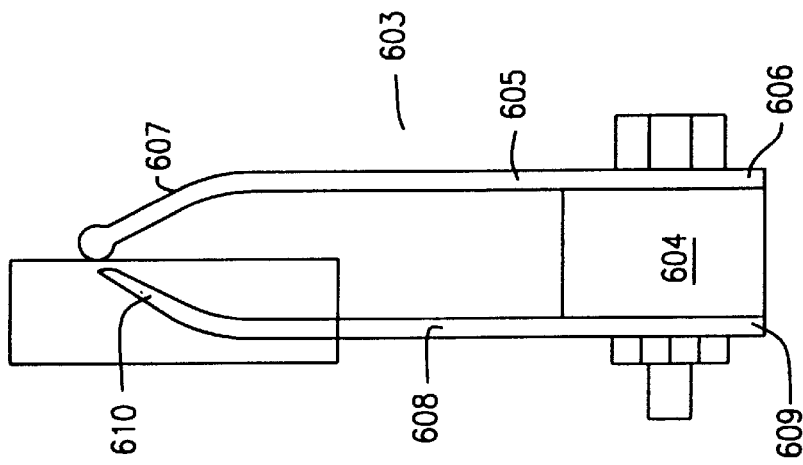
FIG. 47 shows the mount of FIG. 46 with the stent moved in a longitudinal direction.
Figure 46:
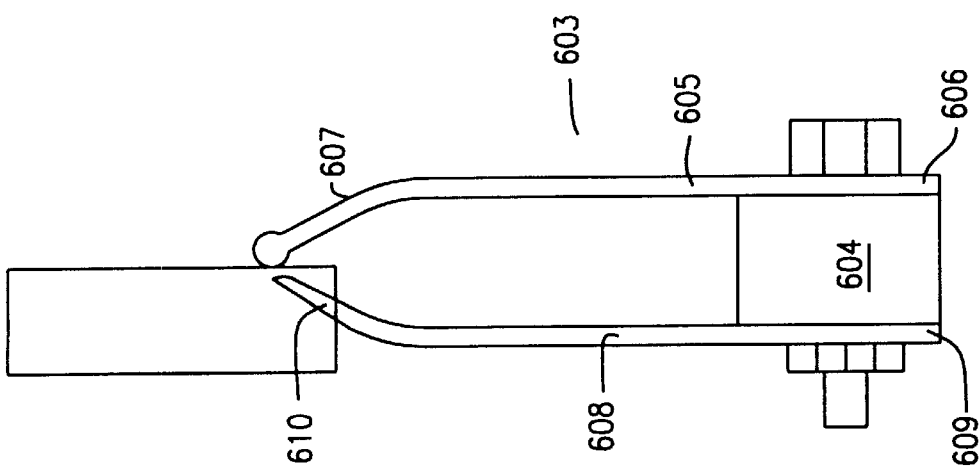
FIG. 46 shows a mount for electropolishing a stent.
Figure 48:
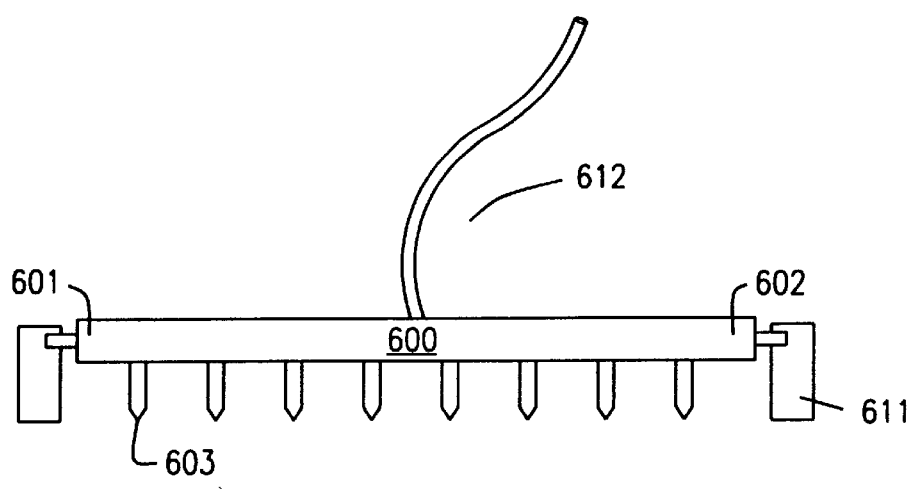
FIG. 48 shows a rack for electropolishing a stent with material to be sacrificed disposed at the ends.

FIGS. 46 to 48 show a jig 612 for electropolishing a tubular stent, comprising a rack 600 having a first end 601 and a second end 602 and provided with a plurality of stent electropolishing mounts 603. Each of the mounts is provided with a base 604 and an electrically conductive first member 605 having a first end 606 connected to the base and a second end 607 adapted to selectively contact the external surface of the tubular stent to be electropolished without damaging its external surface. The mounts are also provided with an electrically non-conductive second member 608 having a first end 609 connected to the base and a second end 610 adapted to be selectively disposed within the longitudinal bore of the stent without damaging the surface defining the longitudinal bore. The first member and the second member are also adapted so as to bias the second end of the second member towards the second end of said first member in an amount sufficient to secure said stent between said first and said second members. The advantage of a mount constructed in accordance with applicants' invention is that the electrically conductive member contacts the external surface of the stent. This reduces the likelihood of undulations and erosion lines occurring on the surface defining the longitudinal bore. These erosion lines frequently occur in stents electropolished utilizing conventional mounts which place the electrically conductive member against the surface defining the longitudinal bore. Electropolishing a stent with Applicants' mount reduces the likelihood that the longitudinal lumen of the stent will have an irregular surface which could result in turbulent fluid flow which could result in thrombosis or platelet aggregation.

In a preferred electropolishing method a stent is placed on a rack constructed as previously discussed. The method comprises immersing the stent in an electropolishing bath and applying electrical current to the first member for a predetermined period of time; and changing the point where the second end of the first member contacts the external surface of the stent prior to the expiration of the predetermined period of time. Changing the point of contact minimizes the concentration of undulations or erosion lines at any given point on the stent near the point of contact of the electrically conductive member. The point of contact may be changed by rotating the stent. In an especially preferred embodiment, the point of contact is changed by varying the distance between the stent and the base by longitudinally moving the stent toward or away from the base as shown in FIGS. 46 and 47. The point of contact is changed at about the midpoint of the predetermined period of time. In an especially preferred embodiment, the treatment is interrupted before the expiration of the predetermined time, the effect of the electropolishing prior to the interruption step is evaluated, and the remaining period of the predetermined time is adjusted to compensate for any variations in the amount of material actually removed prior to the interruption step. The treatment may be interrupted at any time, however, interruption at about the midpoint of the predetermined period of time is preferred.

Pieces of sacrificial material 611 may be added at the first end and the second end of the rack to compensate for the additional material normally removed from stents disposed at the first end and the second end of the rack as shown in FIG. 48. The material is selected and added in an amount sufficient to substantially equalize the amount of additional material normally removed from the stents disposed first and second ends of the rack.

Figure 49:
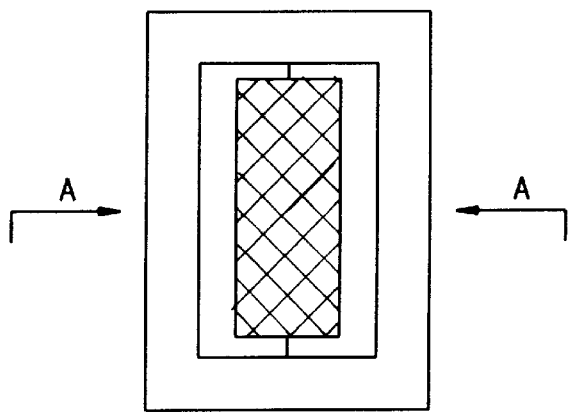
FIG. 49 shows a stent still attached to a metal sheet for electropolishing by attaching an electrode to the sheet.
Figure 50:
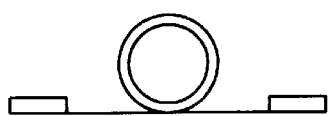
FIG. 50 is a side view of FIG. 49 showing the stent and the remaining portion of the sheet.

In yet another preferred method of electropolishing a stent, the stent is manufactured as previously discussed however, when deforming the pattern into a tubular shape so that said first long side pairs of engagement points contact the second long side pairs of engagement points, a portion of the stent is allowed to remain attached to the sheet of metal, as shown in FIGS. 49 and 50. The bridge is then cut, the engagement points are connected to form the stent, the stent is electropolished by connecting an electrode to the sheet, and the stent is then removed from the sheet. This reduces the likelihood of damage to the stent because the sheet to which the stent is attached is disposable. This method also provides an additional advantage because the disposable sheet to which the stent is attached acts as sacrificial material as previously discussed.

It will be appreciated by persons skilled in the art that the present invention is not limited to what has been particularly shown and described hereinabove. Rather the scope of the present invention is defined only by the claims which follow.

What is claimed is:

1. A sheet for fabricating a stent having a longitudinal lumen comprising:

(a) a flat piece of sheet metal provided with a plurality of stent patterns, each of said patterns having a first long side and a second long side, said first long side provided with a plurality of pairs of engagement points, said second long side provided with a plurality of pairs of engagement points, said plurality of pairs of engagement points disposed substantially opposite each other, said engagement points sized and disposed to communicate when said pattern is deformed and rolled into a tubular shape, each pair of said first long side engagement points provided with a bridge disposed between each first long side engagement point comprising said pair, said bridge having a width that is less than the width of the portions other than said bridge, comprising said stent patterns of said sheet.

2. The sheet of claim 1, wherein said bridge has a width that is about 25% to about 50% of the width of the portions other than said bridge, comprising said stent patterns of said sheet.

3. The sheet of claim 1, wherein said bridge has a width of about 40 microns.

4. The sheet of claim 1, wherein said engagement points are sized and adapted to move in an amount sufficient so as to reduce the likelihood of material stress occurring during welding heating and cooling cycles.

5. The sheet of claim 1, further comprising, additional weld fill material on the side of each of said engagement points substantially opposite said bridge, said weld fill material sized and disposed so as to permit the additional weld fill material to be drawn into a weld point during welding of said engagement points.

6. The sheet of claim 1, further comprising a plurality of alignment apertures disposed in said sheet.

7. The sheet of claim 1, wherein said stent patterns are adapted so that upon expansion of said stent against the internal wall of a vessel substantially no portion of said stent protrudes into said longitudinal lumen of said stent.

* * * * *